United States Patent
Granz

(10) Patent No.: US 11,419,740 B2
(45) Date of Patent: Aug. 23, 2022

(54) ADJUSTABLE SOCKET SYSTEM

(71) Applicant: OSSUR ICELAND EHF, Reykjavik (IS)

(72) Inventor: Dadi Granz, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 138 days.

(21) Appl. No.: 16/018,498

(22) Filed: Jun. 26, 2018

(65) Prior Publication Data
US 2018/0296373 A1     Oct. 18, 2018

Related U.S. Application Data

(63) Continuation-in-part of application No. 15/888,288, filed on Feb. 5, 2018, now Pat. No. 10,806,607.
(Continued)

(51) Int. Cl.
*A61F 2/62* (2006.01)
*A61F 2/80* (2006.01)
(Continued)

(52) U.S. Cl.
CPC .......... *A61F 2/80* (2013.01); *A61F 2/54* (2013.01); *A61F 2/60* (2013.01); *A61F 2/76* (2013.01); *A61F 2/7812* (2013.01); *A61F 2002/502* (2013.01); *A61F 2002/5016* (2013.01); *A61F 2002/5018* (2013.01); *A61F 2002/5021* (2013.01); *A61F 2002/5023* (2013.01); *A61F 2002/5026* (2013.01);
(Continued)

(58) Field of Classification Search
CPC ...... A61F 2002/5018; A61F 2002/5021; A61F 2002/5023

USPC .......................................................... 623/38
See application file for complete search history.

(56) References Cited

U.S. PATENT DOCUMENTS

| 37,282 A | 1/1863 | Engelbrecht et al. |
| 51,593 A | 12/1865 | Jewett |

(Continued)

FOREIGN PATENT DOCUMENTS

| CA | 2854799 A1 | 5/2013 |
| CA | 2889617 A1 | 5/2014 |

(Continued)

OTHER PUBLICATIONS

Alley, "The High-Fidelity Interface: Skeletal Stabilization Through Alternating Soft Tissue Compression and Release", Proceedings of the 2011 MyoElectric Controls/Powered Prosthetics Symposium Frederiction, New Brunswick, Canada, Aug. 2011. 3 Pages.
(Continued)

*Primary Examiner* — David H Willse
(74) *Attorney, Agent, or Firm* — Workman Nydegger

(57) ABSTRACT

A prosthetic connector system for use with a prosthetic socket having a distal end includes a plate defining a plurality of holes and attachable to the distal end of the prosthetic socket. A component is removably attachable to the plate via the plurality of holes and arranged to connect a prosthesis to the prosthetic socket. The plate defines an outer periphery having an asymmetrical configuration contoured to substantially correspond to at least a portion of the component when the component is attached to the plate via at least some of the holes.

12 Claims, 12 Drawing Sheets

Related U.S. Application Data

(60) Provisional application No. 62/455,133, filed on Feb. 6, 2017, provisional application No. 62/458,170, filed on Feb. 13, 2017, provisional application No. 62/597,113, filed on Dec. 11, 2017.

(51) Int. Cl.
  *A61F 2/60* (2006.01)
  *A61F 2/54* (2006.01)
  *A61F 2/78* (2006.01)
  *A61F 2/76* (2006.01)
  *A61F 2/50* (2006.01)

(52) U.S. Cl.
  CPC ............... *A61F 2002/5027* (2013.01); *A61F 2002/5083* (2013.01); *A61F 2002/5084* (2013.01); *A61F 2002/762* (2013.01); *A61F 2002/7695* (2013.01); *A61F 2002/785* (2013.01); *A61F 2002/7862* (2013.01); *A61F 2002/7881* (2013.01); *A61F 2002/7887* (2013.01)

(56) References Cited

U.S. PATENT DOCUMENTS

| | | |
|---|---|---|
| 366,494 A | 7/1887 | Marks |
| 470,431 A | 3/1892 | Marks |
| 1,066,605 A | 7/1913 | Hanger |
| 1,082,256 A | 12/1913 | Apgar |
| 1,144,681 A | 6/1915 | Apgar |
| 1,861,311 A | 5/1932 | Logan |
| 1,893,853 A | 1/1933 | Tullis |
| 2,025,835 A | 12/1935 | Trautman |
| 2,229,728 A | 1/1941 | Eddels |
| 2,634,424 A | 4/1953 | O'Gorman |
| 2,669,728 A | 2/1954 | Ritchie |
| 2,759,271 A | 8/1956 | Von Duyke |
| 2,908,016 A | 10/1959 | Botko |
| 2,949,674 A | 8/1960 | Wexler |
| 3,678,587 A | 7/1972 | Madden |
| 4,128,903 A | 12/1978 | Marsh et al. |
| 4,161,042 A | 7/1979 | Cottingham et al. |
| 4,225,982 A | 10/1980 | Cochrane et al. |
| 4,268,922 A | 5/1981 | Marsh et al. |
| 4,283,800 A | 8/1981 | Wilson |
| 4,300,245 A | 11/1981 | Saunders |
| 4,459,709 A | 7/1984 | Leal et al. |
| 4,704,129 A | 11/1987 | Massey |
| 4,715,124 A | 12/1987 | Harrington |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,938,775 A | 7/1990 | Morgan |
| 4,988,360 A | 1/1991 | Shamp |
| 5,003,969 A | 4/1991 | Azer et al. |
| 5,014,441 A | 5/1991 | Pratt |
| 5,108,456 A | 4/1992 | Coonan, III |
| 5,133,777 A | 7/1992 | Arbogast et al. |
| 5,168,635 A | 12/1992 | Hoffman |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,424,782 A | 6/1995 | Aoki |
| 5,503,543 A | 4/1996 | Laghi |
| 5,520,529 A | 5/1996 | Heckel |
| 5,529,575 A | 6/1996 | Klotz |
| 5,529,576 A | 6/1996 | Lundt et al. |
| 5,545,231 A | 8/1996 | Houser |
| 5,571,209 A | 11/1996 | Brown, Sr. |
| 5,651,792 A | 7/1997 | Telikicherla |
| 5,652,053 A | 7/1997 | Liegeois |
| 5,653,766 A | 8/1997 | Naser |
| 5,718,925 A | 2/1998 | Kristinsson et al. |
| 5,724,714 A | 3/1998 | Love |
| 5,728,165 A | 3/1998 | Brown, Sr. |
| 5,800,565 A | 9/1998 | Biedermann |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Slemker |
| 5,867,517 A | 4/1999 | Laghi |
| 6,033,440 A | 3/2000 | Schall et al. |
| 6,051,026 A | 4/2000 | Biedermann et al. |
| 6,077,300 A | 6/2000 | Sabolich et al. |
| 6,206,932 B1 | 3/2001 | Johnson |
| 6,228,124 B1 | 5/2001 | Slemker et al. |
| 6,231,618 B1 | 5/2001 | Schall et al. |
| 6,238,437 B1 * | 5/2001 | Johnson ............. A61F 2/66 623/27 |
| 6,334,876 B1 | 1/2002 | Perkins |
| 6,368,357 B1 | 4/2002 | Schon et al. |
| 6,406,499 B1 | 6/2002 | Kania |
| 6,444,282 B1 | 9/2002 | Shirer |
| 6,458,163 B1 | 10/2002 | Slemker et al. |
| 6,497,028 B1 | 12/2002 | Rothschild et al. |
| 6,500,210 B1 | 12/2002 | Sabolich et al. |
| 6,557,177 B2 | 5/2003 | Hochmuth |
| 6,669,736 B2 | 12/2003 | Slemker et al. |
| 6,700,563 B1 | 3/2004 | Koizumi |
| 6,761,743 B1 | 7/2004 | Johnson |
| 6,793,682 B1 | 9/2004 | Mantelmacher |
| 6,942,703 B2 | 9/2005 | Carstens |
| 6,974,484 B2 | 12/2005 | Caspers |
| 6,991,657 B1 | 1/2006 | Price, Jr. |
| 7,090,700 B2 | 8/2006 | Curtis |
| 7,094,212 B2 | 8/2006 | Karason et al. |
| 7,097,799 B1 | 8/2006 | Burton |
| 7,105,122 B2 | 9/2006 | Karason |
| 7,118,602 B2 | 10/2006 | Bjarnason |
| 7,172,714 B2 | 2/2007 | Jacobson |
| 7,240,414 B2 | 7/2007 | Taylor, Sr. |
| 7,288,116 B2 | 10/2007 | Ikeda |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,402,265 B2 | 7/2008 | Jacobson |
| 7,479,163 B2 | 1/2009 | Slemker et al. |
| 7,488,349 B2 | 2/2009 | Einarsson |
| 7,591,857 B2 | 9/2009 | Slemker et al. |
| 7,658,720 B2 | 2/2010 | Johnson, III |
| 7,727,284 B2 | 6/2010 | Warila |
| 7,753,866 B2 | 7/2010 | Jackovitch |
| 7,762,973 B2 | 7/2010 | Einarsson et al. |
| 7,867,286 B2 | 1/2011 | Einarsson |
| 7,980,921 B2 | 7/2011 | Saravanos |
| 7,985,192 B2 | 7/2011 | Sheehan et al. |
| 8,007,544 B2 | 8/2011 | Jonsson et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,123,818 B2 | 2/2012 | Bjarnason et al. |
| 8,142,517 B2 | 3/2012 | Horie |
| 8,303,527 B2 | 11/2012 | Joseph |
| 8,308,815 B2 | 11/2012 | Mccarthy |
| 8,323,353 B1 | 12/2012 | Alley et al. |
| 8,382,852 B2 | 2/2013 | Laghi |
| 8,403,993 B2 | 3/2013 | Aram et al. |
| 8,414,658 B2 | 4/2013 | Johnson et al. |
| 8,470,050 B2 | 6/2013 | Dillingham |
| 8,480,758 B2 | 7/2013 | McLeod |
| 8,491,667 B2 | 7/2013 | Dillingham |
| 8,535,389 B2 | 9/2013 | Mckinney |
| 8,576,250 B2 | 11/2013 | Sabiston et al. |
| 8,656,918 B1 | 2/2014 | Alley et al. |
| 8,795,385 B2 | 8/2014 | Bache |
| 8,845,755 B2 | 9/2014 | Dillingham |
| 8,978,224 B2 | 3/2015 | Hurley et al. |
| 9,044,349 B2 | 6/2015 | Hurley et al. |
| 9,050,202 B2 | 6/2015 | Bache et al. |
| 9,248,033 B2 | 2/2016 | Bache |

(56) References Cited

U.S. PATENT DOCUMENTS

| | | | |
|---|---|---|---|
| 9,283,093 B2 | 3/2016 | Alley | |
| 9,468,542 B2 | 10/2016 | Hurley et al. | |
| 9,468,543 B2 | 10/2016 | Hurley et al. | |
| 9,474,633 B2 | 10/2016 | Williams et al. | |
| 9,504,585 B2 | 11/2016 | Cornell | |
| 9,549,828 B2 | 1/2017 | Hurley et al. | |
| D778,452 S | 2/2017 | Cespedes et al. | |
| 9,572,691 B2 | 2/2017 | Pacanowsky et al. | |
| 10,123,886 B2* | 11/2018 | Palmer | A61F 2/66 |
| 10,172,728 B2 | 1/2019 | Hurley et al. | |
| 10,179,056 B2 | 1/2019 | Hurley et al. | |
| 10,206,795 B2 | 2/2019 | Pedtke et al. | |
| 10,765,537 B2* | 9/2020 | Smith | B25J 17/0241 |
| 2002/0087216 A1* | 7/2002 | Atkinson | A61F 2/6607 623/38 |
| 2002/0099450 A1 | 7/2002 | Dean, Jr. et al. | |
| 2003/0181990 A1 | 9/2003 | Phillips | |
| 2004/0260402 A1 | 12/2004 | Baldini et al. | |
| 2005/0209706 A1 | 9/2005 | Warila | |
| 2005/0216096 A1 | 9/2005 | Wagman | |
| 2005/0267600 A1 | 12/2005 | Haberman et al. | |
| 2005/0278039 A1 | 12/2005 | Nobbe | |
| 2005/0288798 A1 | 12/2005 | Curtis | |
| 2006/0009860 A1 | 1/2006 | Price, Jr. | |
| 2006/0020348 A1 | 1/2006 | Slemker et al. | |
| 2006/0135902 A1 | 6/2006 | Ingimundarson et al. | |
| 2007/0004993 A1 | 1/2007 | Coppens et al. | |
| 2007/0078523 A1 | 4/2007 | Kholwadwala et al. | |
| 2007/0152379 A1 | 7/2007 | Jacobson | |
| 2007/0298075 A1 | 12/2007 | Borgia et al. | |
| 2008/0066272 A1 | 3/2008 | Hammerslag et al. | |
| 2008/0269914 A1 | 10/2008 | Coppens et al. | |
| 2009/0036999 A1 | 2/2009 | Egilsson et al. | |
| 2009/0076625 A1 | 3/2009 | Groves et al. | |
| 2009/0105844 A1 | 4/2009 | Ortiz | |
| 2009/0240344 A1 | 9/2009 | Colvin et al. | |
| 2009/0287128 A1 | 11/2009 | Ingimundarson et al. | |
| 2009/0299490 A1 | 12/2009 | Summit | |
| 2010/0030344 A1 | 2/2010 | Hansen et al. | |
| 2010/0036300 A1 | 2/2010 | Sheehan et al. | |
| 2010/0036505 A1 | 2/2010 | Hassler | |
| 2010/0082116 A1 | 4/2010 | Johnson et al. | |
| 2010/0121464 A1 | 5/2010 | Mantelmacher | |
| 2010/0160722 A1 | 6/2010 | Kuyava et al. | |
| 2010/0191348 A1 | 7/2010 | Kettwig et al. | |
| 2010/0274364 A1 | 10/2010 | Pacanowsky et al. | |
| 2011/0029096 A1 | 2/2011 | Laghi | |
| 2011/0035027 A1 | 2/2011 | Mccarthy | |
| 2011/0071647 A1 | 3/2011 | Mahon | |
| 2011/0114635 A1 | 5/2011 | Sheehan | |
| 2011/0232837 A9 | 9/2011 | Ottleben | |
| 2011/0320010 A1 | 12/2011 | Vo | |
| 2012/0022667 A1 | 1/2012 | Accini et al. | |
| 2012/0041567 A1 | 2/2012 | Cornell | |
| 2012/0095570 A1 | 4/2012 | Marquette | |
| 2012/0101417 A1 | 4/2012 | Joseph | |
| 2012/0101597 A1 | 4/2012 | Bache | |
| 2012/0143077 A1 | 6/2012 | Sanders et al. | |
| 2012/0165956 A1 | 6/2012 | Li | |
| 2012/0191218 A1 | 7/2012 | Mccarthy | |
| 2012/0215324 A1 | 8/2012 | King | |
| 2012/0253475 A1 | 10/2012 | Kelley et al. | |
| 2012/0259432 A1 | 10/2012 | Dillingham | |
| 2012/0259434 A1 | 10/2012 | Dillingham | |
| 2012/0271210 A1 | 10/2012 | Galea et al. | |
| 2012/0271433 A1 | 10/2012 | Galea et al. | |
| 2012/0283846 A1 | 11/2012 | Janssen et al. | |
| 2012/0293411 A1 | 11/2012 | Leithinger et al. | |
| 2013/0123940 A1 | 5/2013 | Hurley et al. | |
| 2013/0192071 A1 | 8/2013 | Esposito et al. | |
| 2013/0197318 A1 | 8/2013 | Herr et al. | |
| 2013/0218296 A1 | 8/2013 | Koniuk et al. | |
| 2013/0245785 A1 | 9/2013 | Accini et al. | |
| 2013/0282141 A1 | 10/2013 | Herr et al. | |
| 2014/0031953 A1 | 1/2014 | Mackenzie | |
| 2014/0121783 A1 | 5/2014 | Alley | |
| 2014/0135946 A1 | 5/2014 | Hurley et al. | |
| 2014/0149082 A1 | 5/2014 | Sanders et al. | |
| 2014/0227584 A1 | 9/2014 | Hurley et al. | |
| 2014/0277584 A1* | 9/2014 | Hurley | A61F 2/5044 623/33 |
| 2014/0277585 A1 | 9/2014 | Kelley et al. | |
| 2015/0018974 A1 | 1/2015 | Dillingham | |
| 2015/0105867 A1 | 4/2015 | Novak | |
| 2015/0168943 A1 | 6/2015 | Hurley et al. | |
| 2015/0190252 A1 | 6/2015 | Hurley et al. | |
| 2015/0230945 A1 | 8/2015 | Bache et al. | |
| 2015/0257905 A1 | 9/2015 | Bache | |
| 2015/0265434 A1 | 9/2015 | Hurley et al. | |
| 2015/0313729 A1 | 11/2015 | Williams et al. | |
| 2015/0313730 A1 | 11/2015 | Hurley et al. | |
| 2015/0352775 A1 | 12/2015 | Geshlider et al. | |
| 2016/0000586 A1 | 1/2016 | Hurley et al. | |
| 2016/0000587 A1 | 1/2016 | Hurley et al. | |
| 2016/0045340 A1* | 2/2016 | Vaughan | A61F 2/80 623/33 |
| 2016/0058584 A1 | 3/2016 | Cespedes et al. | |
| 2016/0143752 A1 | 5/2016 | Hurley et al. | |
| 2016/0158035 A1 | 6/2016 | Alley | |
| 2016/0235560 A1 | 8/2016 | Cespedes et al. | |
| 2016/0278949 A1 | 9/2016 | Dillingham | |
| 2016/0331562 A1 | 11/2016 | Bache et al. | |
| 2016/0334780 A1 | 11/2016 | Dair et al. | |
| 2016/0338858 A1 | 11/2016 | Hurley et al. | |
| 2017/0027718 A1 | 2/2017 | Williams et al. | |
| 2017/0128238 A1 | 5/2017 | Hurley et al. | |
| 2017/0156896 A1 | 6/2017 | Alley | |
| 2018/0000615 A1 | 1/2018 | Hurley et al. | |
| 2018/0008434 A1 | 1/2018 | Geiger et al. | |
| 2018/0020973 A1 | 1/2018 | Hurley et al. | |
| 2018/0021153 A1 | 1/2018 | Hurley et al. | |
| 2018/0153716 A1 | 6/2018 | Martin | |
| 2018/0221178 A1 | 8/2018 | Steinberg et al. | |
| 2018/0221179 A1 | 8/2018 | Bache et al. | |
| 2018/0263702 A1 | 9/2018 | Hurley et al. | |
| 2018/0303637 A1 | 10/2018 | Bache et al. | |
| 2018/0333279 A1 | 11/2018 | Granz et al. | |

FOREIGN PATENT DOCUMENTS

| | | | |
|---|---|---|---|
| CN | 104884005 A | 9/2015 | |
| CN | 104053416 B | 11/2016 | |
| CN | 106913407 A | 7/2017 | |
| CN | 109328045 A | 2/2019 | |
| DE | 319623 C | 3/1920 | |
| DE | 19529055 A1 | 1/1997 | |
| DE | 102014001000 A1 | 7/2014 | |
| DE | 10 2017 131 319 A1 * | 6/2019 | A61F 2/62 |
| EP | 0204407 A2 | 12/1986 | |
| EP | 0269391 A2 | 6/1998 | |
| EP | 1433447 A2 | 6/2004 | |
| EP | 1656911 A1 | 5/2006 | |
| EP | 2866747 B1 | 2/2017 | |
| GB | 127 451 A | 6/1919 | |
| GB | 675811 A | 7/1952 | |
| GB | 2080114 A | 2/1982 | |
| GB | 2169207 A | 7/1986 | |
| JP | 8-294504 A * | 11/1996 | A61F 2/60 |
| RU | 2088182 C1 | 8/1997 | |
| WO | 91/16019 A1 | 10/1991 | |
| WO | 98/12994 A1 | 4/1998 | |
| WO | 0003665 A1 | 1/2000 | |
| WO | 0030572 A1 | 6/2000 | |
| WO | 2007/035875 A2 | 3/2007 | |
| WO | 2008/116025 A2 | 9/2008 | |
| WO | 2009/093020 A2 | 7/2009 | |
| WO | 2012/021823 A1 | 2/2012 | |
| WO | 2012054700 A1 | 4/2012 | |
| WO | 2013/071308 A1 | 5/2013 | |
| WO | 2014004709 A1 | 1/2014 | |
| WO | 2014005071 A1 | 1/2014 | |
| WO | 2014068269 A1 | 5/2014 | |
| WO | 2014070666 A1 | 5/2014 | |
| WO | 2014153244 A1 | 9/2014 | |

(56) References Cited

FOREIGN PATENT DOCUMENTS

| WO | 2014205403 A1 | 12/2014 |
|---|---|---|
| WO | 2015095232 A1 | 6/2015 |
| WO | 2015143249 A1 | 9/2015 |
| WO | 2016183065 A1 | 11/2016 |
| WO | 2017186901 A1 | 11/2017 |
| WO | 2017186902 A1 | 11/2017 |
| WO | 2017194479 A1 | 11/2017 |
| WO | 2018017959 A1 | 1/2018 |

OTHER PUBLICATIONS

Andrysek, "Lower-Limb Prosthetic Technologies in the Developing World: A Review of Literature from 1994-2010", Prosthetics and Orthotics International, Cardiff, Wales, UK; vol. 34, No. 4, Dec. 2010; pp. 378-398.
Conn, "Materials Science: A Look at Some of the Substances on the Market for Device Fabrication", O&P Almanac, Jun. 2012, pp. 28-31; http://wwww.allardusa.com/pdf/articles/Materials%20Science%20Article%20-%20June%202012%20O%26P%20Almanac.pdf.
Fairley, M. "From Academia to the Developing World: Student Engineers Create Collaborative Technologies", The O&P Edge Magazine, OandP.com, Mar. 2011, pp. 1-9. Downloaded from http://www.oandp.com/articles/2011-05-03.asp.
Fairley, M. "M.A.S. Socket: A Transfemoral Revolution", The O&P Edge, Jun. 2004, www.oandp.com/articles/2004-06_03.asp. 5 Pages.
"COMFIL—Thermo Formable Composite Technique", Fillaur LLC and Centri, Fabrication Manuel, Jun. 15, 2012, pp. 1-13.
Gard, S.A. "Overview of Lower Limb Prosthetics Research", WRAMC and the VA Orthopedic & Prosthetic Workshop Arlington, VA, Nov. 17-18, 2003, pp. 1-49.
Geil, M.D., "Consistency, Precision, and Accuracy of Optical and Electromagnetic Shape-Capturing Systems for Digital Measurement of Residual-limb Anthropometries of Persons With Transtibial Amputation", Journal of Rehabilitation Research and Development, vol. 44, No. 4, 2007; pp. 515-524.
Gleave, "A Plastic Socket and Stump Casting Technique for Above-Knee Prostheses", Orthopaedic and Prosthetic Appliance Department, Hong Kong Government Medical Department, The Journal of Bone and Joint Surgery, vol. 47B, No. 1, Feb. 1965, pp. 100-103.
Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. 1 page.
Greenwald, et al., "Volume Management: Smart Variable Geometry Socket (SVGS) Technology for Lower-Limb Prostheses", American Academy of Orthotists & Prosthetists, vol. 15, No. 3, 2003, pp. 107-112.
Hwang, "Blooming Winner—Spark!", Spark Galleries, 2012/Spark/Concept,Spark Design Awards, 2012 3 Pages. Downloaded from http://www.sparkawards.com/galleriew/index.cfm?entry=9525D900-EoEF-59BD-46597D99 . . . .
Jana, "Designing a Cheaper, Simpler Prosthetic Arm", ZDNet, Nov. 14, 2011, pp. 1-5. Downloaded from http://www.2dnet.com/article/designing-a-cheaper-simpler-prosthetic-arm/.
Koike, et al., "The TC Double Socket Above-knee Prosthesis", Prosthetics and Orthotics International, vol. 5, 1981 pp. 129-134.
Krouskop, et al., "Computer-aided design of a prosthetic socket for an above-knee amputee", Journal of Rehabilitation Research and Development, vol. 24, No. 2 1987, pp. 31-38.
Manucharian, "An Investigation of Comfort Level Trend Differences Between the Hands-On Patellar Tendon Bearing and Hands-Off Hydrocast Transtibial Prosthetic Sockets", JPO: American academy of Orthotists & Prosthetists, Washington, D.C., U.S.A.; vol. 23, No. 3, 2011: pp. 124-140.

Otto Bock Healthcare LLP, "Initial and Interim Prostheses", Otto Bock Healthcare LLP, Prosthetics Lower Extremities 2008, Feb. 2013 pp. 1-8, www.ottobockus.com/cps/rde/xbcr/ob_us_en/08cat_1.pdf.
Sanders, et al., "Residual limb volume change: Systematic review of measurement and management", Journal of Rehabilitation Research & Development, 2011, vol. 48, No. 8, pp. 949-986.
Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 27, No. 1; pp. 71-74.
SBIR topic summary: "Pro-Active Dynamic Accommodating Socket", http://www.dodsbir.net/sitis/archieves_display_topic.asp?Bookmark=34570; downloaded Mar. 25, 2013, U.S. A. 3 pages.
Smith, "Silver Linings for O&P Devices", The Academy Today, vol. 1, No. 4: Oct. 2005, 4 Pages, Downloaded from, http://www.oandp.org/AcademyTODAY/20050ct/7 .asp.
Spaeth, JP , "Laser Imaging and Computer-Aided Design and Computer-Aided Manufacture in Prosthetics and Orthotics", Physical Medicine and Rehabilitation Clinics of North America, Elsevier Publishing, Amsterdam, The Netherlands; Feb. 2006 pp. 245-263, Abstract. 2 pages.
Turner, "FIT for Everyone", Yanko Design-Form Beyond Junction, Jul. 17, 2015, pp. 1-10. Downloaded from http://www.yankodesign.com/2013/07/17/fit-for-erveryone/.
"Hanger ComfortFlex Socket System for Prosthetic Devices:" Downloaded Nov. 28, 2012 from http://www.hanger.com/prosthetics/services/Technology/Pages/ComfortFlex.asp pp. 1-2.
Wilson JR. "A Material for Direct Forming of Prosthetic Sockets", Artificial Limbs., vol. 4, No. 1, 1970, Downloaded from http://www.oandplibrary.org/al/1970_01_053.asp; downloaded Dec. 14, 2012. pp. 53-56.
Wilson, "Recent Advances in Above-Knee Prosthetics", Artificial Limbs, vol. 12, No. 2, 1968 pp. 1-27.
Wu, et al, "CIR sand casting system for trans-tibial socket", Prosthetics and Orthotics International, Aug. 2003: vol. 27, pp. 146-152.
Quigley, Michael, "Prosthetic Management: Overview, Methods and Materials," Chapter 4, Atlas of Limb Prosthetics: Surgical, Prosthetic, and Rehabilitation Principles, Second Edition, 1992, 10 Pages. Downloaded from: http://www.pandplibrary.org/alp/chapot-01.asp.
Burgess, et al. "Immediate Post-Surgical Prosthetic Fitting", The Management of Lower-Extremity Amputations, Aug. 1969, pp. 42-51.
Compton, et al., "New Plastics for Forming Directly on the Patient", Prosthetics and Orthotics International, 1978, vol. 2, No. 1, pp. 43-47, Abstract. 3 Pages.
Fairley, "Socket Can Be Fabricated, Modified, Fitted—In One Hour", The O&P Edge, Jun. 2007. 5 Pages.
"Cut-4-Custom: Custom TLSO in Less Than an Hour", The O&P Edge, Oct. 2010. 2 Pages.
"Remoldable Prosthetics", InstaMorph Moldable Plastic, http://instamorph.com/wp-content/uploads/legcast1.png, Retrieved, May 10, 2016. 3 Pages.
International Search Report from PCT Application No. PCT/US2019/037663, dated Oct. 2, 2019.
International Search Report from PCT Application No. PCT/US2019/036267, dated Sep. 30, 2019.
Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.
Manual: "Socket Evaluation System with the Rapid Adjustment Pylon", [retrieved from the internet on May 22, 2014], <URL:http://www.fillauer.com>; 4 pages.

* cited by examiner

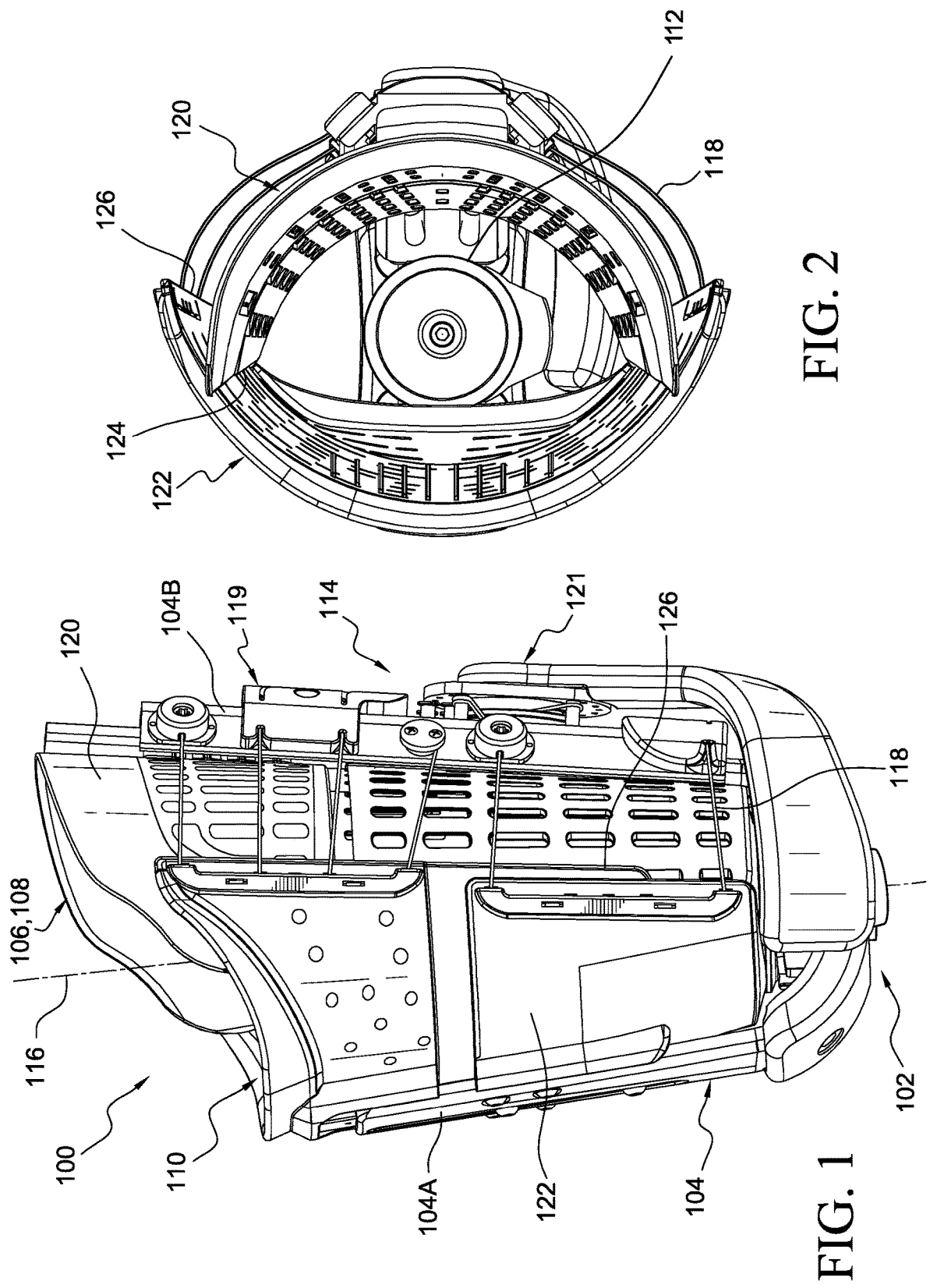

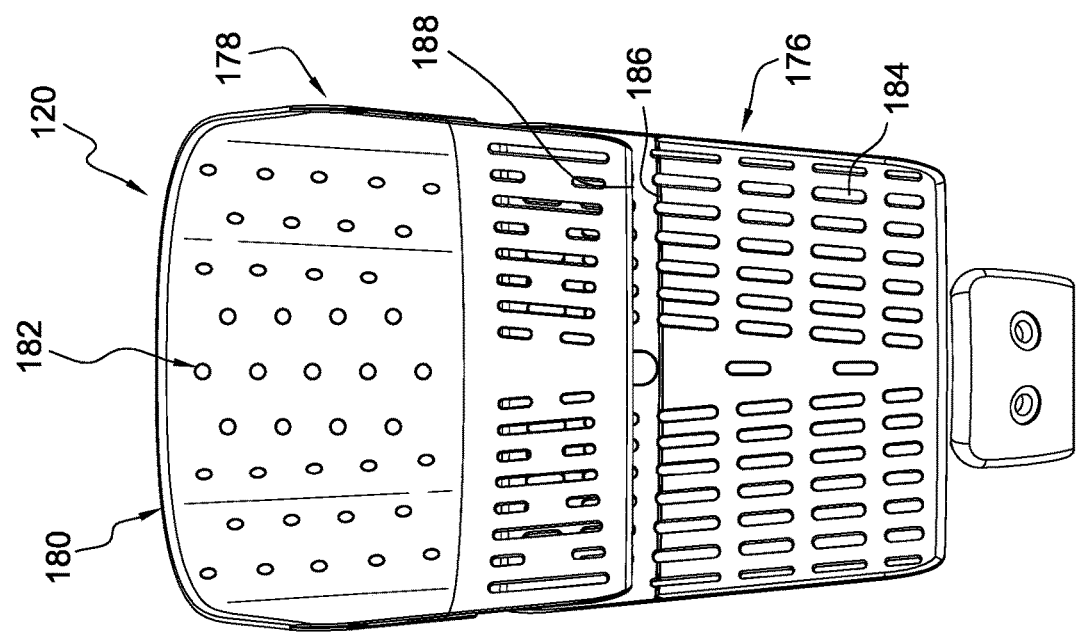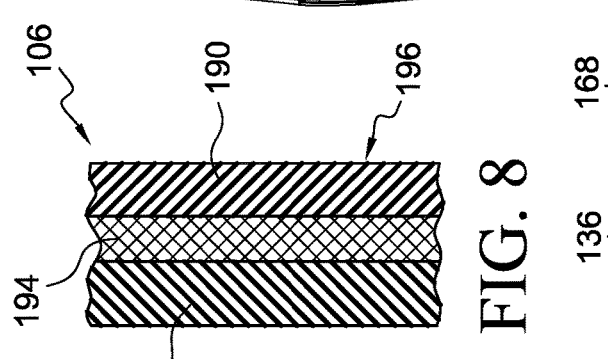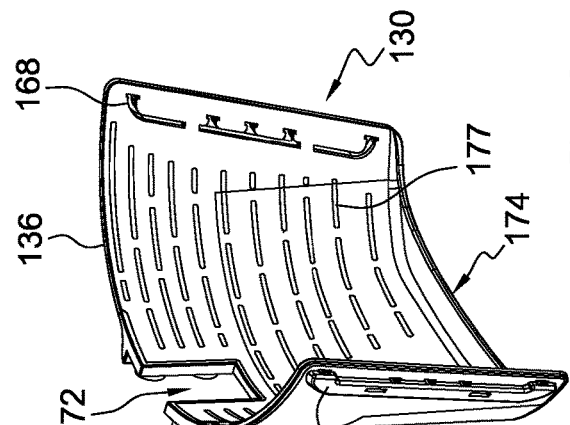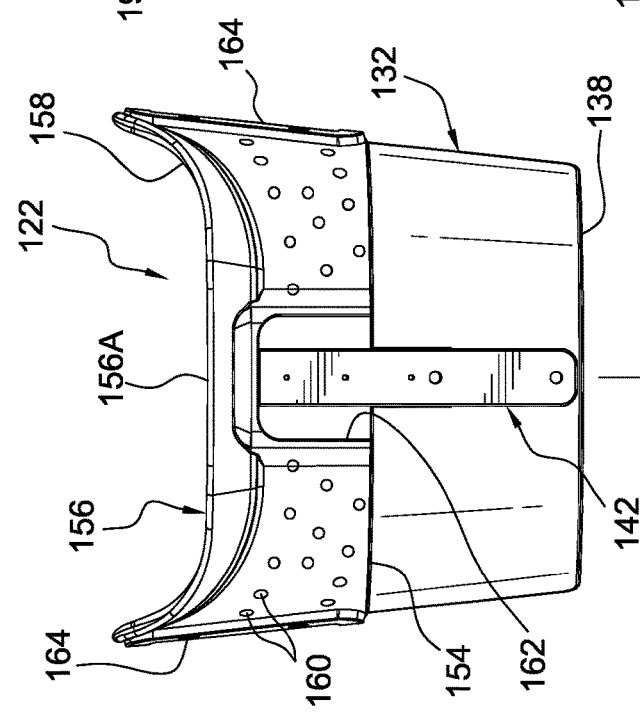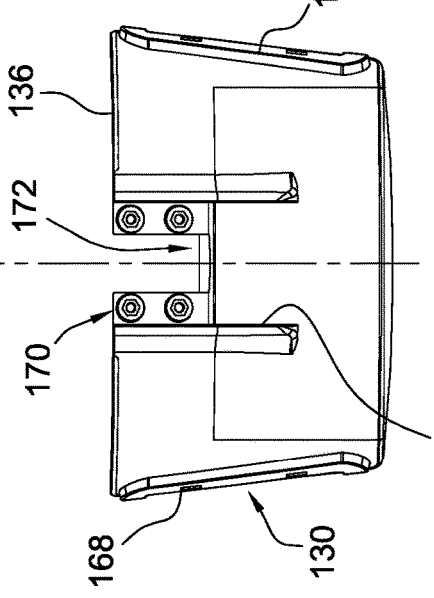

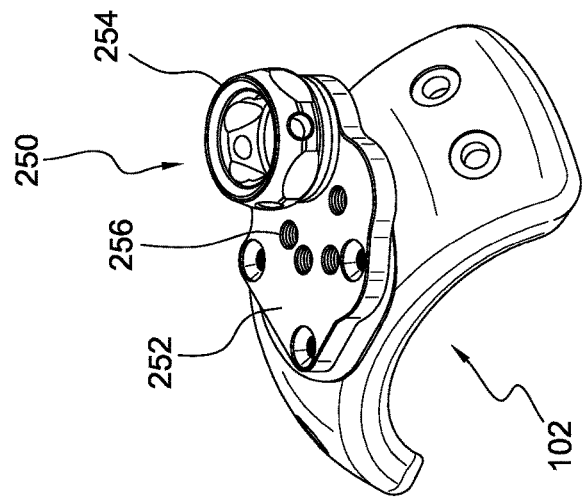
FIG. 10
FIG. 12
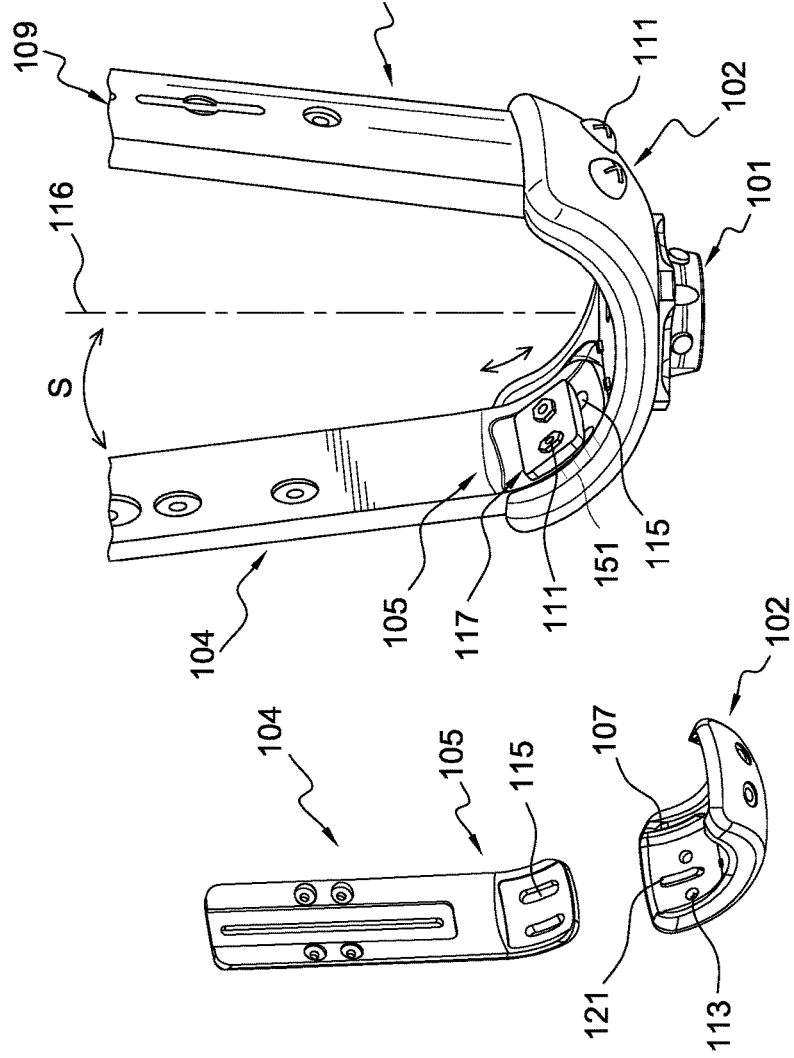
FIG. 11
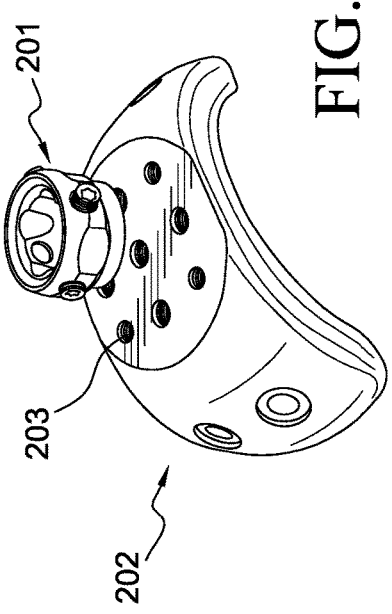
FIG. 9

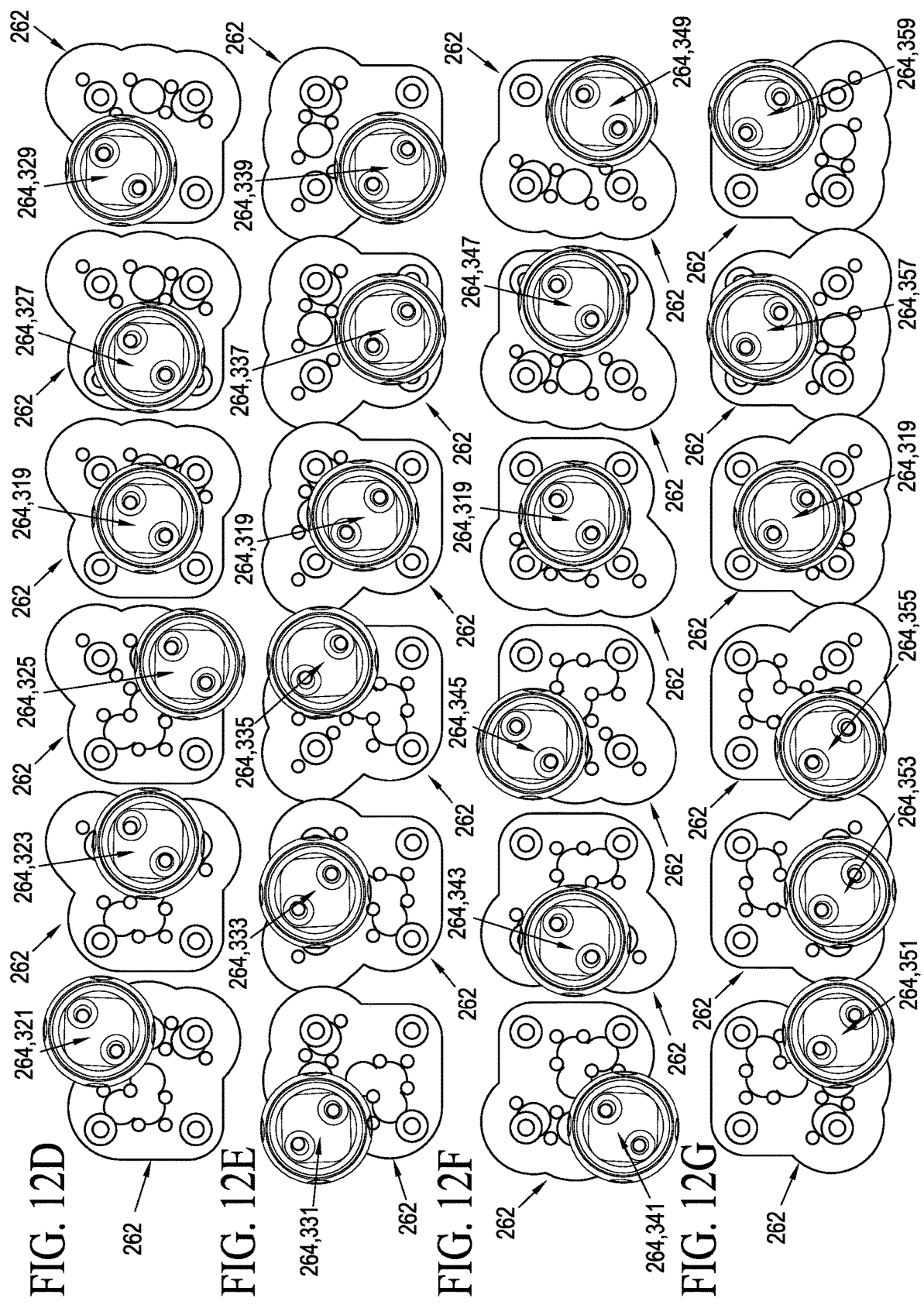

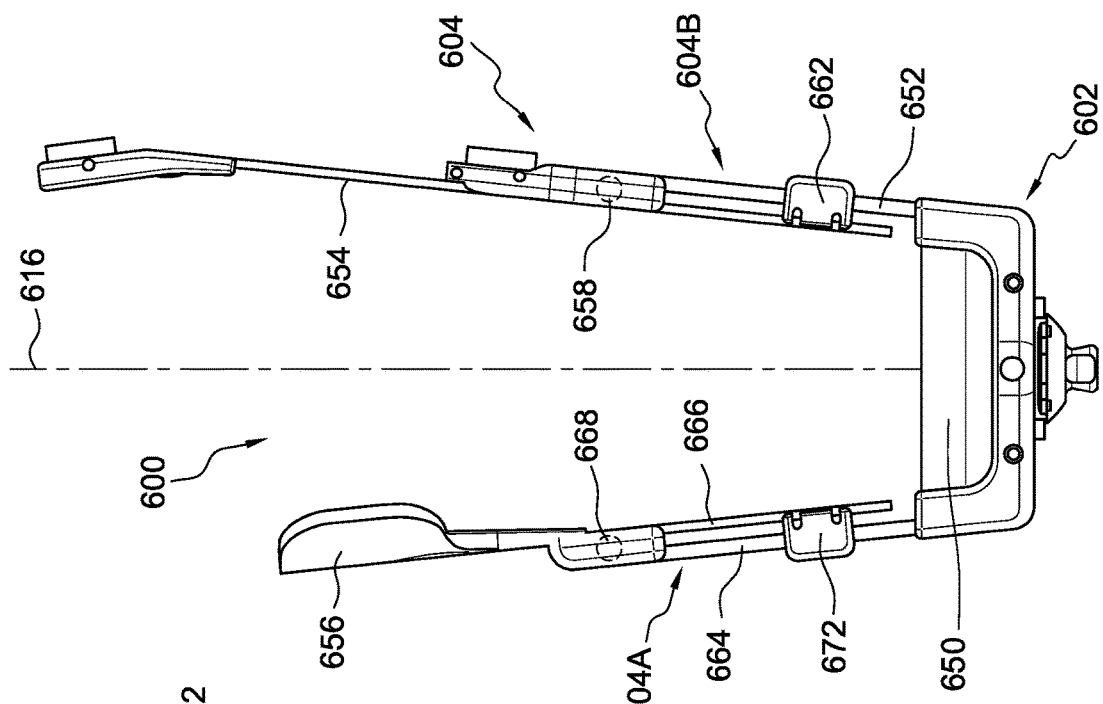
FIG. 16
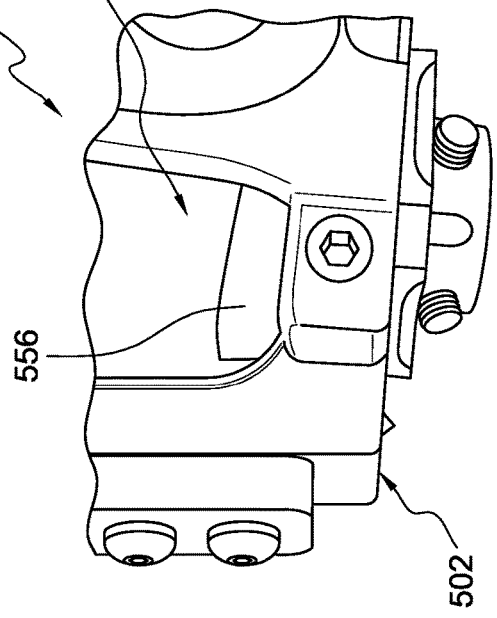
FIG. 15A
FIG. 15B

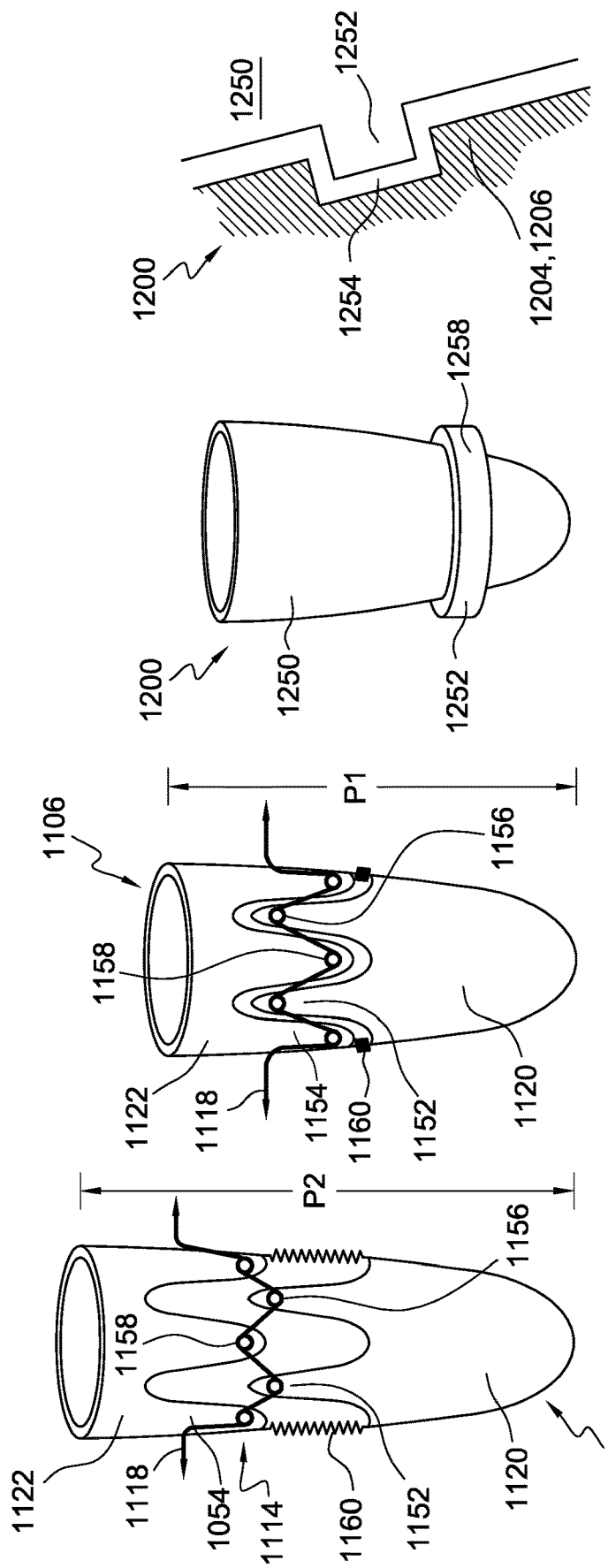

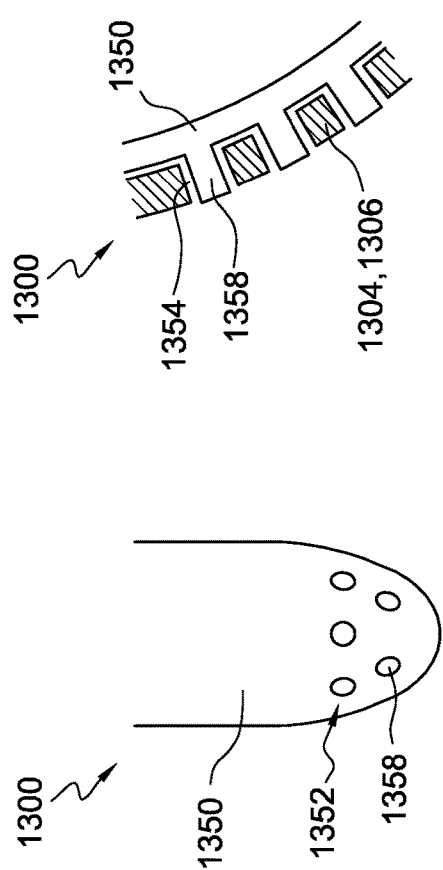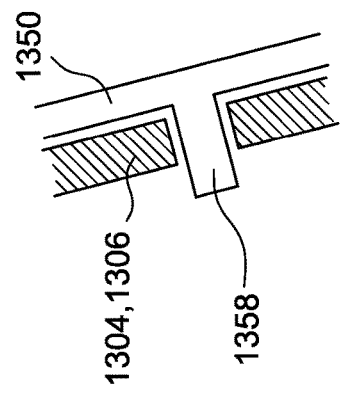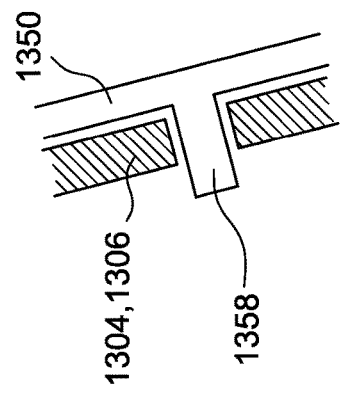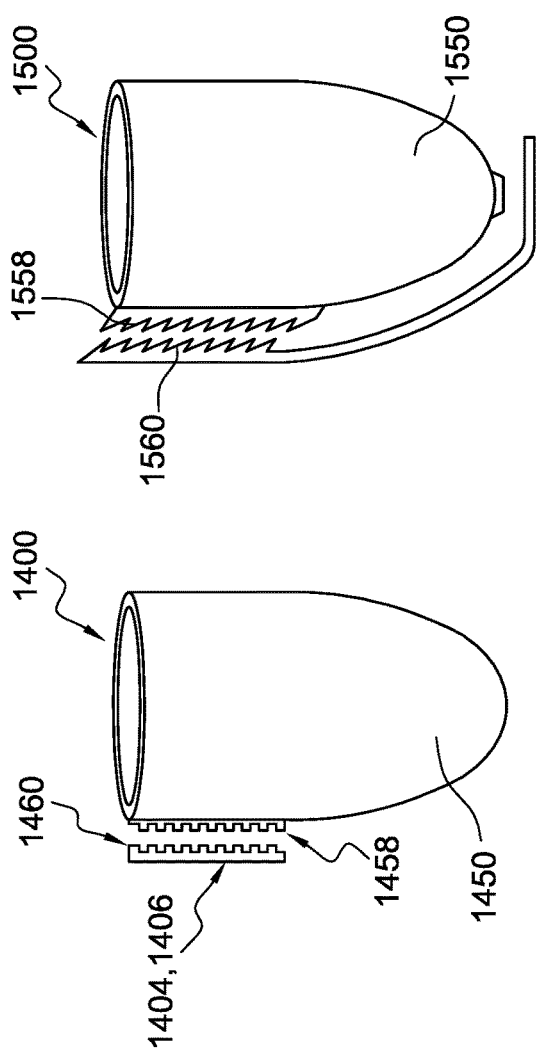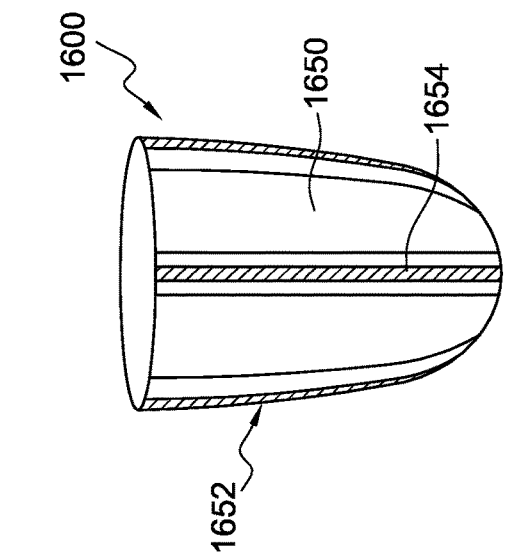

ADJUSTABLE SOCKET SYSTEM

TECHNICAL FIELD

The disclosure relates to an adjustable socket system for a residual limb.

BACKGROUND

A typical prosthetic leg and foot include a socket, pylon, and foot. A socket is commonly referred to as the portion of a prosthesis that fits around and envelops a residual limb or stump, and to which prosthetic components, such as a foot, are attached. Fitting and alignment of the socket are difficult tasks to perform, and require extensive knowledge, training and skill for the prosthetist.

The socket must fit closely to the stump to provide a firm connection and support, but must also be sufficiently loose to allow for circulation. In combination with proper fitting, the socket must transfer loads from the residual limb to the ground in a comfortable manner.

Conventional sockets are rigid and generally have a general uniform shape which receives a large portion of the residual limb. These sockets are permanently formed to a customized shape that is static, meaning the socket does not account for shape and volume fluctuations of the residual limb. When there are shape and volume fluctuations, the fitting of the socket is impeded, with these sockets causing discomfort, pain and soft tissue breakdown of the stump. Conventional sockets also tend to be bulky and cumbersome to wear, and may be difficult to don, making the residual limb uncomfortable when worn.

Some attempts have been made to develop adjustable sockets with individual components that can be varied to account for volume and shape fluctuations of the residual limb. Such sockets, however, tend to have poor force distribution on the residual limb, causing a concentration of pressure on certain areas of the residual limb. This poor distribution of pressures causes pain, discomfort, and even tissue breakdown. Such sockets also tend to provide unsatisfactory support and suspension. They also can necessitate massive inventories of components, increasing expense and space requirements.

SUMMARY

Conventional sockets are known to inadequately account for shape and volume fluctuations of a residual limb. They also tend to be bulky and cumbersome to wear. Known adjustable socket systems may better accommodate shape and volume fluctuations than conventional sockets but tend to be uncomfortable and provide inadequate support and suspension. There is thus a need for an adjustable socket that can both comfortably accommodate shape and volume fluctuations of the residual limb, and provide improved support and stability.

Embodiments of the present disclosure comprise an adjustable socket system that provides superior structure adjustment features over prior art adjustable socket systems. From its versatility in fitting and force distribution, the adjustable socket system can decrease discomfort and improve support and stability over known adjustable sockets. Moreover, it will be appreciated that the adjustable socket systems of the present disclosure may be adapted to a variety of different types of amputations, whether configured for the leg or arm.

The adjustable socket system of the present disclosure can include a base, longitudinal supports connected to the base and extending along a longitudinal axis, and shell components operatively connected to the longitudinal supports and defining a receiving volume adapted to receive a residual limb. The adjustable socket system is movable between an open configuration in which at least one of the shell components is moved radially outward relative to the longitudinal axis to loosen the fit of the adjustable socket system, and a closed configuration in which at least one of the shell components is moved radially inward relative to the open configuration to secure the fit of the adjustable socket system on the residual limb.

The shell components include a first shell component having distal and proximal parts that are longitudinally displaceable with respect to one another such that a length of the first shell component is adjustable between a first length, and a second length different than the first length. By adjusting the relative longitudinal positions between the distal and proximal parts, the shell components can better accommodate residual limbs of different lengths. It also advantageously improves the fit, stability, and support provided by the system over prior art adjustable socket systems.

According to a variation, an overlap is defined between the proximal and distal parts along the longitudinal axis. As the overlap between the distal and proximal parts varies the contact surface between the first shell component and the residual limb varies. This allows the contact surface area of the first shell component to structurally or physically adapt to the length of the residual limb, improving the force distribution and fit of the adjustable socket system.

This is advantageous over prior art systems including supports that simply reposition the same contact area at different heights using adjustable struts, providing inadequate force distribution and stability. The adjustable length of the shell component is also beneficial because it does not require a large inventory of parts that have to be interchanged to fit and support different lengths of the residual limbs as in the prior art.

BRIEF DESCRIPTION OF THE DRAWINGS

These and other features, aspects, and advantages of the present disclosure will become better understood regarding the following description, appended claims, and accompanying drawings.

FIG. 1 is a side view of an adjustable socket system according to an embodiment.

FIG. 2 is a top view of the adjustable socket system in FIG. 1.

FIG. 5 is an exploded view of a shell component according to an embodiment.

FIG. 6 is a perspective view of the distal part of the shell component in FIG. 5.

FIG. 7 is a side view of another shell component according to an embodiment.

FIG. 8 is a cross section of a shell component according to another embodiment.

FIG. 9 is an exploded view of a longitudinal support and base according to an embodiment.

FIG. 10 is an assembled view of the longitudinal support and base in FIG. 9.

FIG. 11 is a bottom view of a base according to another embodiment.

FIG. 12 is a bottom view of a base according to another embodiment.

FIG. 12D shows alternative attachment locations of the prosthetic adaptor on the plate of FIG. 12A in a first orientation.

FIG. 12E shows alternative attachment locations of the prosthetic adaptor on the plate of FIG. 12A in a second orientation.

FIG. 12F shows alternative attachment locations of the prosthetic adaptor on the plate of FIG. 12A in a third orientation.

FIG. 12G shows alternative attachment locations of the prosthetic adaptor on the plate of FIG. 12A in a fourth orientation.

FIG. 15A is a side view of a distal insert according to an embodiment.

FIG. 15B is a side view of the distal insert of FIG. 15A inserted in an adjustable socket system.

FIG. 16 is a side view of an adjustable socket system according to another embodiment.

FIG. 21A is a side view of an adjustable socket system in a second predetermined length according to another embodiment.

FIG. 21B is a side view of the adjustable socket system of FIG. 21A in a first predetermined length.

FIG. 22A is a side view of an adjustable socket system according to another embodiment.

FIG. 22B is a detailed view of the adjustable socket system of FIG. 22A.

FIG. 23A is a side view of an adjustable socket system according to another embodiment.

FIG. 23B is a detailed view of the adjustable socket system in FIG. 23A.

FIG. 23C is a detailed side view of the adjustable socket system of FIG. 23A.

FIG. 24 is a side view of an adjustable socket system according to another embodiment.

FIG. 25 is a side view of an adjustable socket system according to another embodiment.

FIG. 26 is a side view of an adjustable socket system according to another embodiment.

DETAILED DESCRIPTION OF VARIOUS EMBODIMENTS

Figure 4A:
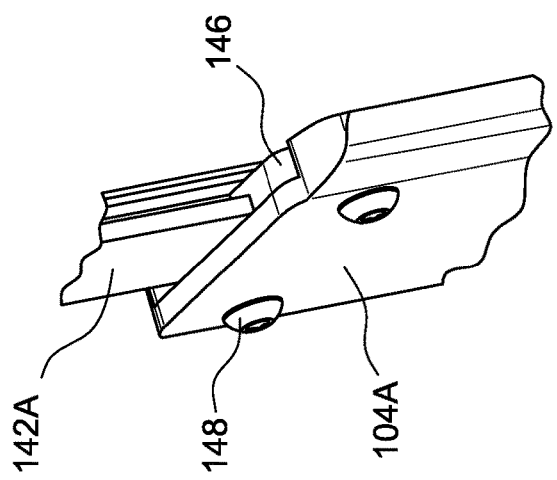
FIG. 4A is a perspective view of a longitudinal support according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112(f).

FIGS. 1 and 2 illustrate an adjustable socket system 100 according to an embodiment including a base 102, a plurality of longitudinal supports 104 connected to the base 102, and a plurality of shell components 106 connected to the longitudinal supports 104. The shell components 106 collectively form a socket wall 108 defining a receiving volume 110 adapted to receive a residual limb. The base 102 is arranged to provide support for a distal end of the residual limb and can include at least one coupling device 112 (shown in FIG. 2) for fixing or securing the residual limb or a liner to the base 102. The longitudinal supports 104 are shown comprising elongate medial and lateral supports 104A, 104B, but can be in any suitable configuration.

The adjustable socket system 100 is radially adjustable between an open configuration and a closed configuration. In the open configuration, at least some of the longitudinal supports 104 and/or shell components 106 are free to move or are forced radially outward relative to a longitudinal axis 116 of the adjustable socket system 100, increasing the receiving volume 110 or increasing a circumference of the adjustable socket system 100. This effectively loosens the fit of the adjustable socket system 100 on a residual limb inserted in the receiving volume 110, or decreases the loading on the residual limb from the socket wall 108.

In the closed configuration, at least some of the longitudinal supports 104 and/or the shell components 106 are moved or forced radially inward relative to the open configuration, decreasing the receiving volume 110 or decreasing the circumference of the adjustable socket system 100. For instance, the longitudinal supports 104 can comprise a medial support 104A having an elongate configuration and a lateral support 104B having an elongate configuration.

At least one of the medial or lateral supports 104A, 104B can be pivotally connected to the base 102 such that in the closed configuration at least one of the supports 104A, 104B is folded or rotated toward the other to decrease the receiving volume 110. This tightens the fit of the adjustable socket system 100 on a residual limb inserted in the receiving volume 110 and/or increases the loading on the residual limb from the socket wall 108. It will be appreciated that movement of any portion of a longitudinal support 104 or shell component 106 can move the adjustable socket system 100 between the open and closed configurations. In other embodiments, at least one of the longitudinal supports 104 has a non-articulating configuration adapted to bend or flex in order to adjust or vary the receiving volume 110.

A tightening system 114 is arranged to move the adjustable socket system 100 between the open and closed configurations. The tightening system 114 includes at least one tensioning element 118, a plurality of guides 119 accommodating and directing the at least one tensioning element 118, and a tensioning unit 121 operatively linked to the at least one tensioning element 118. When the tensioning unit 121 is moved to an on position, a corresponding tensioning element 118 is longitudinally displaced, increasing tension in the at least one tensioning element 118. This causes at least the lateral support 104B and/or the shell components 106 to move toward the closed configuration, tightening or securing the fit of the adjustable socket system 100 on the residual limb. When the tensioning unit 121 is moved to an off position, the at least one tensioning element 118 can return toward its original position, decreasing tension in the tensioning element 118. This allows the longitudinal supports 104 and/or the shell components 106 to move toward the open configuration, loosening the fit of the adjustable socket system 100.

The shell component 106 can include a first shell component 122 that wraps around and engages at least a medial aspect of the residual limb and a second shell component 120 that wraps around and engages at least a lateral aspect of the residual limb. The first and second shell components 122, 120 can be configured differently. The first shell component 122 can extend or wrap around a substantial portion of the circumference of the adjustable socket system 100.

The second shell component 120 can wrap from a lateral side to a medial side, terminating at a medial or trailing edge 124. The first shell component 122 can wrap from a medial side to a lateral side, terminating at a lateral or leading edge 126. According to a variation, an upper edge of the first shell component 122 can extend upwardly toward the leading edge 126 such that a reduced height of the first shell component 122 is formed along the medial aspect of the residual limb. This beneficially improves comfort by reducing the likelihood of interference between the first shell component 122 and a user's unaffected limb and/or other body part.

As seen in FIG. 2, the first and second shell components 122, 120 overlap one another in a circumferential direction in at least the closed configuration. In an embodiment, a portion of an inner surface of the first shell component 122 can overlap a portion of an outer surface of the second shell component 120 to form a circumferential overlap between the trailing and leading edges 124, 126. As the adjustable socket system 100 moves between the closed and open configurations, the circumferential overlap between the first and second shell components 122, 120 varies, which, in turn, beneficially permits volume adjustment within a volume range. The circumferential overlap also permits improved pressure distribution from the adjustable socket system 100 onto the residual limb during use and thus a better fit. This reduces the likelihood of soft tissue from bulging out or escaping out of the adjustable socket system 100, increasing user comfort.

Figure 3B:
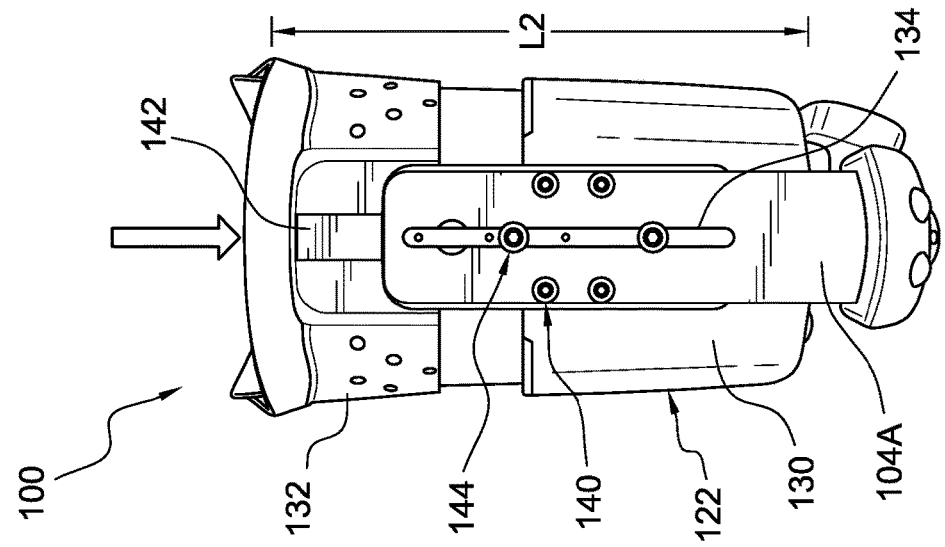
FIG. 3B is another side view of the adjustable socket system in FIG. 1.
Figure 3A:
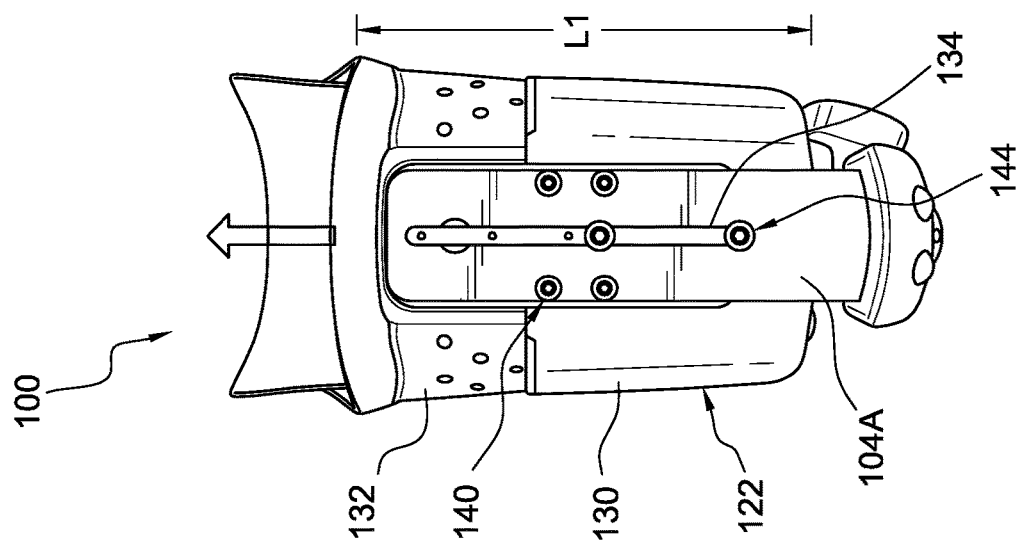
FIG. 3A is a side view of the adjustable socket system in FIG. 1.

Referring now to FIGS. 3A and 3B, at least one of the shell components 106 has an adjustable height, improving the fit, stability, and support provided by the adjustable socket system 100 over prior art adjustable socket systems.

For instance, the first shell component 122 can include a distal part 130 and a proximal part 132 that are arranged to be longitudinally displaceable with respect to one another, so that they can be adjusted and fixed in relation to one another either continuously or in a step-adjustable manner. By adjusting the relative longitudinal position between the distal and proximal parts 130, 132, a change of length of the first shell component 122 can be achieved in order to better accommodate residual limbs of different lengths.

A reduction of a length of the first shell component 122 can be achieved by moving the proximal part 132 toward the distal part 130 along the medial support 104A as shown in FIG. 3A. An increase of the length of the first shell component 122 can be achieved by moving the proximal part 132 away from the distal part 130 along the medial support 104A as shown in FIG. 3B. Adjusting the relative longitudinal position between distal and proximal parts 130, 132 can thus adjust the length of the first shell component 122 between a first predetermined length L1 (shown in FIG. 3A) and a second predetermined length L2 (shown in FIG. 3B). It also allows the adjustable socket system 100 to accommodate longitudinal supports 104 of different heights or lengths. It can also adapt or adjust the desired load on the residual limb.

As seen, the distal part 130 and the proximal part 132 overlap one another in a longitudinal direction, defining an overlap between a proximal end 136 (shown in FIG. 5) of the distal part 130 and a distal end 138 (shown in FIG. 5) of the proximal part 132. This longitudinal overlap helps ensure that there are no or minimal longitudinal gaps between the distal part 130 and the proximal part 132 as the first shell component 122 supports a residual limb during use.

The size of the overlap increases as the proximal part 132 moves toward the distal part 130 along the medial support 104A, which, in turn, shortens the length of the first shell component 122 and moves it toward the first predetermined length L1. The length or size of the overlap decreases as the proximal part 132 moves away from the distal part 130 along the medial support 104A, which, in turn, increases the length of the first shell component 122 and moves it toward the second predetermined length L2.

As the overlap between the distal and proximal parts 130, 132 varies, the contact surface area between the first shell component 122 and the residual limb varies. For example, the first shell component 122 can continuously engage and support the residual limb between the first and second predetermined lengths L1, L2. As the overlap decreases, the contact surface between the first shell component 122 and the residual limb increases. As the overlap increases, the contact surface between the first shell component 122 and the residual limb decreases. This advantageously allows the contact surface area of the first shell component 122 to physically and structurally adapt to the length of the residual limb, improving the force distribution and fit of the adjustable socket system 100. If a user's residual limb is taller or longer, the length and contact surface of the first shell component 122 can be lengthened or increased by sliding the proximal part 132 away from the distal part 130 along the medial support 104A to account for the greater length. If a user's residual limb is shorter, the length and contact surface area of the first shell component 122 can be shortened or decreased by sliding the proximal part 132 toward the distal part 130 along the medial support 104A to account for the shorter length.

This is advantageous over prior art systems including supports that simply reposition the same contact area at different heights using adjustable struts, providing inadequate force distribution and stability. The adjustable length of the first shell component 122 is also beneficial because it does not require a large inventory of parts that have to be interchanged to fit and support different lengths of the residual limbs as in the prior art.

It will be appreciated that the distal and proximal parts 130, 132 of the first shell component 122 can be operatively connected to one another in any suitable manner. For instance, the proximal part 132 can be slidably attached to the medial support 104A via an elongate slot 134. In an embodiment, the distal part 130 is attached to the medial support 104A via a plurality of fasteners 140 and medial support 104A defines the elongate slot 134. A stiffening member 142 on the proximal support 132 is attached to the medial support 104A via a plurality of fasteners 144 extending through the elongate slot 134, which, in turn, slidably attach the proximal part 132 to the medial support 104A. This sliding attachment allows for continuous adjustment of the longitudinal position of the proximal part 132 relative to the distal part 130 along the length of the elongate slot 134. The length of the elongate slot 134 can in part define the first and second predetermined lengths L1, L2 of the first shell component 122.

In use, the fasteners 144 can be manipulated to selectively lock and unlock the longitudinal position of the proximal part 132 relative to the distal part 130. To fix or lock the longitudinal position of the proximal part 132 relative to the distal part 130, the fasteners 144 can be tightened to clamp the stiffening member 142 to the medial support 104A. To adjust the longitudinal position of the proximal part 132 relative to the distal part 130, the fasteners 144 can be loosened to unclamp the stiffening member 142 from the medial support 104A, which, in turn, allows the proximal part 132 to slide up and down within the elongate slot 134. This beneficially permits the length of the first shell component 122 to adjust between the first and second predetermined lengths L1, L2, better accommodating residual limbs of different lengths.

The outer surface of the proximal part 132 is shown slidably engaging the inner surface of the distal part 130 however in other embodiments the inner surface of the proximal part 132 can slidably engage the outer surface of the distal part 130 as the first shell component 122 adjusts in length.

Figure 4B:
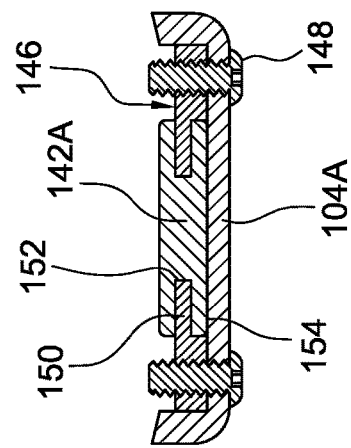
FIG. 4B is a cross section of the longitudinal support shown in FIG. 4A.

FIGS. 4A and 4B illustrate an alternative connection between the distal and proximal parts 130, 132 according to another embodiment. Similar to the previous embodiment, the distal part 130 is attached to the medial support 104A and the proximal part 132 is attached to a stiffening member 142A. A clamping plate 146 is attached to the medial support 104A via a plurality of fasteners 148 and to the stiffening member 142A via protrusions 150 of the clamping plate 146 slidably located within corresponding guides or tracks 152 formed on the stiffening member 142A. The clamping plate 146 and the stiffening member 142A are located within a recess 154 defined along a posterior aspect of the medial support 104A.

In use, the fasteners 148 can be manipulated to selectively lock and unlock the longitudinal position of the stiffening member 142A (and proximal part 132) relative to the medial support 104A (and distal part 130). To fix or lock the longitudinal position of the proximal part 132 relative to the distal part 130, the fasteners 148 can be tightened to clamp the stiffening member 142A between the clamping plate 146 and the medial support 104A. To adjust the longitudinal position of the proximal part 132 relative to the distal part 130, the fasteners 148 can be loosened to unclamp the stiffening member 142A from the medial support 104A, allowing the proximal part 132 to slide up and down within the tracks 152.

FIGS. 5 and 6 illustrate the first shell component 122 in additional detail. The first shell component 122 includes the distal part 130 and the proximal part 132 arranged to overlap one another in a longitudinal direction. The overlap between the distal and proximal parts 130, 132 is generally defined between the proximal end 136 of the distal part 130 and the distal end 138 of the proximal part 132.

A shoulder or abutment 154 is defined along the outer surface of the proximal part 132. The shoulder 154 can extend in a transverse direction across the proximal part 132. The proximal part 132 can move toward the distal part 130 until the proximal end 136 of the distal part 130 reaches or substantially reaches the shoulder 154. The shoulder 154 can thus provide a stop or limit to longitudinal movement between the distal and proximal parts 130, 132 in a direction toward the first predetermined length L1 (shown in FIG. 3A). It can also offer an index or indicator so that a user or clinician adjusting the height or length of the first shell component 122 can tell whether the first shell component 122 has been fully moved to the first predetermined length L1.

The distal and proximal parts 130, 132 can be contoured to generally correspond to the residual limb and can have a flexibility to bend and shape to the residual limb and a stiffness to distribute forces from the tightening system 114 and create stability in the adjustable socket system 100. Exemplary suitable materials for forming the distal and proximal parts 130, 132 can include plastic materials, such as thermoplastic or thermosetting polymers, fiber reinforced plastic, polypropylene, polyethylene, molded chopped fibers, or any other suitable materials. In an embodiment, the material forming the distal and proximal parts 130, 132 can include antimicrobial and/or ultraviolet protection additives.

As seen, the proximal part 132 includes a flexible edge 156 on the proximal aspect. The flexible edge 156 is arranged to bend or flex when the user's residual limb exerts a force on the flexible edge 156. This has the effect of reducing the likelihood of creating a pressure point on the residual limb from the proximal part 132 and can provide pressure relief to the residual limb, improving the comfort and effectiveness of the adjustable socket system 100. The flexible edge 156 can extend along some or all of a width of the proximal aspect. Optionally, an end section 156A can angle, curve, or extend away from the other portions of the flexible edge 156 or the residual limb, spacing the end section 156A a distance away from the residual limb. Because the end section 156A extends away from the residual limb, the residual limb can bend or flex the flexible edge 156 further away from the proximal part 132 as the residual limb pushes against the flexible edge 156, reducing pressure points or edge pressures on the residual limb from the proximal part 132.

The flexible edge 156 can be formed via overmolding a different material onto the proximal aspect of the proximal part 132. For instance, the flexible edge 156 can be formed via a flexible plastic or elastomer, such as, for example, thermoplastic elastomer (TPE) or other suitable material. In other embodiments, the flexible edge 156 can be formed by a thinner portion of the proximal part 132. In other embodiments, the flexible edge 156 can be removably attached to the proximal part 132 so that it can be easily removed for replacement and/or cleaning. This can improve versatility of the adjustable socket system 100 and/or user hygiene. For instance, the flexible edge 156 can be selected from an inventory of flexible edge components having a range durometers so that the flexible edge 156 can be selected and attached to the proximal part 132 based on user preference, activity, and/or other criteria.

According to a variation, the proximal part 132 includes an interface region 158 along an inner surface of the proximal part 132. The interface region 158 can include one or more materials with a high coefficient of friction such as elastomeric polymers to increase friction or suspension between the proximal part 132 and the residual limb. The interaction between the interface region 158 and the residual limb can help control transverse rotation, pistoning, or other unwanted movement between the proximal part 132 and the residual limb. The interface region 158 can also provide additional cushioning to the residual limb, improving user comfort. In an embodiment, the interface region 158 is overmolded on the proximal part 132 over a plurality of apertures 160 in the proximal part 132, mechanically fastening the interface region 158 to the proximal part 132. In an embodiment, the material forming the flexible edge 156 (e.g., TPE) can extend distally a distance along an inner surface of the proximal part 132 to form the interface region 158.

An outer surface of the proximal part 132 defines a receptacle 162 extending in a longitudinal direction for the medial support 104A. The receptacle 162 can be arranged to generally correspond to the configuration of the medial support 104A.

The stiffening member 142 is shown attached to the proximal part 132 within the receptacle 162 and extending in a longitudinal direction along the outer surface of the proximal part 132. The stiffening member 142 can be over-molded on the proximal part 132 or attached in any other suitable manner. The stiffening member 142 and the proximal part 132 can have a same length or a different length. The stiffening member 142 can extend between the distal end 138 of the proximal part 132 and a closed end of a receptacle 162. The stiffening member 142 can be formed of metal, aluminum, plastic, carbon fiber, combinations thereof, or any other suitable material.

A plurality of guides 164 are located on the outer surface of the proximal part 132 at or near the leading edge 126 of the first shell component 122. The guides 164 can be integral to the proximal part 132, lowing the overall profile of the adjustable socket system 100. The guides 164 are shown having an elongate or c-shape that directs a tensioning element 118 along a length of the leading edge 126.

Referring now to the distal part 130, its outer surface includes a receptacle 166 for the medial support 104A and a plurality of guides 168 for tensioning elements 118 of the tightening system 114 at or near the leading edge 126. As seen, the guides 168 can extend along substantially the entire height or length of the proximal part 132, which, in turn, helps the tensioning elements 118 more evenly tension the shell components 106. A plurality of fastener holes 170 are arranged for receiving fasteners 140 to attach the distal part 130 to the medial support 104A. Optionally, a cutout 172 is formed in the proximal edge 136 between the fastener holes 170.

Referring to FIG. 6, a lip 174 extends radially inward and circumferentially from a distal aspect of the distal part 130. The lip 174 is arranged to be compressed against the residual limb when the adjustable socket system 100 is donned. This helps the adjustable socket system 100 better conform to the residual limb and minimizes movement of the adjustable socket system 100 relative to the residual limb during use.

The lip 174 can be formed via a flexible plastic or elastomer, such as, for example, thermoplastic elastomer (TPE) or other suitable material.

According to a variation, the inner surface of the distal part 130 can include one or more features to help control transverse rotation, pistoning, or other unwanted movement between the distal part 130 and the residual limb. For instance, the inner surface of the distal part 130 can include cuts 177, crushable ribs, or bosses.

FIG. 7 illustrates the second shell component 120 according to an embodiment. The second shell component 120 includes a distal part 176 and a proximal part 178 attached to the lateral support 104B. The distal and proximal parts 176, 178 overlap one another and are arranged to be longitudinally displaceable with respect to one another, similar to the distal and proximal parts 130, 132 of the first shell component 122. The outer surface of the proximal part 178 is shown slidably engaging the inner surface of the distal part 176; however, in other embodiments the inner surface of the proximal part 178 can slidably engage the outer surface of the distal part 176.

Similar to the first shell component 122, the proximal part 178 of the second shell component 120 can slide along the lateral support 104B (shown in FIG. 1) to longitudinally displace the proximal part 178 relative to the distal part 176. In other embodiments, the proximal part 178 can be repositioned relative to the distal part 176 by lengthening and shortening the lateral support 104B. Optionally, at least one of the longitudinal supports 104 can be interchangeable with different supports having varying configurations. For instance, the lateral support 104B can be selected from an inventory of longitudinal supports comprising a standard length telescoping support and a longer telescoping strut that is interchangeable with the standard telescoping support, providing varying lengths of the longitudinal supports 104 and/or amounts of longitudinal displacement between the overlapping shell parts without undesirably sacrificing stability of the adjustable socket system 100.

The distal and proximal parts 176, 178 can be contoured to generally correspond to the residual limb and can have a flexibility to bend and shape to the residual limb, and a stiffness to distribute forces from the tightening system 114 and create stability in the adjustable socket system 100. The distal and proximal parts 176, 178 can be made of the same materials as the first shell component 122. As seen, the second shell component 120 has a greater length than the first shell component 122.

The proximal part 178 can include an interface region 180 arranged to form an interface between the residual limb and the proximal part 178. The interface region 180 can be located along a proximal region of the proximal part 178 and formed of TPE or other suitable material. One or more bosses 182 can be arranged on the inner surface of the proximal part 178 to help control transverse motion, pistoning, and/or other unwanted motion between the proximal part 178 and the residual limb. The bosses 182 are shown within the interface region 180 but can be located on any suitable portion of the proximal part 178. According to a variation, the distal and proximal parts 176, 178 define a plurality of elongate slots 184 to help provide transverse motion control and ventilation.

According to a variation, a shoulder or abutment 186 can be defined along the inner surface of the distal part 176. The shoulder 186 can extend in a transverse direction across the distal part 176. The proximal part 178 can move toward the distal part 176 until a distal end 188 of the proximal part 178 reaches or substantially reaches the shoulder 186, providing a stop or index for a user or clinician.

FIG. 8 is a cross section of a shell component 106 according to an embodiment. The shell component 106 can include an inner layer 190, an outer layer 192, and a semi-rigid or rigid body 194 between the inner and outer layers 190 and 192. The inner layer 190 can define an inner surface of the shell component 106. The inner layer 190 can include a rubber or elastomer material. The inner layer 190 can be a textile layer and can be skin friendly. The inner layer 190 can include padding or cushioning material to increase user comfort. The outer layer 192 can define an outer surface of the shell component 106. The outer layer 192 can comprise a robust or durable material. The outer layer 192 can comprise a fabric or textile material arranged to form an anchor for the guides and to resist failure under tension from the tensioning elements.

The inner and outer layers 190, 192 can comprise a textile sleeve 196 defining a pocket arranged to receive the body 194. The body 194 can be repeatedly removable from the sleeve 196. This advantageously can allow the body 194 to be removed from the sleeve 196 such that the sleeve 196 can be washed and/or repaired. The body 194 can be attached to the sleeve 196 via adhesives, magnets, hook and loop systems, or any other suitable method.

FIG. 9 shows the base 102 and a longitudinal support 104 in an exploded configuration and FIG. 10 shows the base 102 and longitudinal supports 104 in an assembled configuration. The base 102 can have a concave shape or any other suitable shape for supporting a distal end of a residual limb.

The longitudinal supports 104 are removably attached to the base 102 via one or more fasteners 111. As discussed above, at least one of the longitudinal supports 104 can flex or bend relative to the base 102 or it can be attached to the base 102 in a pivoting or folding manner. The base 102 and longitudinal supports 104 can be formed of any suitable material. For example, the base 102 and/or distal end portions 105 of the longitudinal supports 104 can comprise molded parts including plastic with carbon fiber mixed therein. This beneficially reduces the weight and cost of the adjustable socket system 100.

The angle of at least one of the longitudinal supports 104 relative to the longitudinal axis 116 can be adjustable via the connection between the longitudinal support 104 and the base 102. The upper surface of the base 102 defines at least one seat 107 arranged to generally correspond to the configuration of the distal end portion 105 of the longitudinal support 104. Particularly, the seat 107 defines a curvature generally corresponding to a curvature of an outer surface of the distal end portion 105, such that as the distal end portion 105 is moved distally along the seat 107, an angle S between a proximal portion 109 of the longitudinal support 104 and the longitudinal axis 116 increases. As the distal end portion 105 is moved proximally along the seat 107, the angle S decreases. The angle of the longitudinal support 104 relative to the longitudinal axis 116 is thus adjustable by adjusting the position of the distal end portion 105 along the seat 107. The curvature and/or length of the seat 107 can define in part a range of angular adjustment for the longitudinal support 104.

The distal end portion 105 can be attachable to the base 102 via a pair of fasteners 111 extending through a pair of through-holes 113 in the base 102 and a pair of elongated through-holes 115 in the distal end portion 105 of the support 104. The elongated through-holes 115 beneficially enable a continuous adjustment of the position of the distal end portion 105 relative to the base 102 along the length of the through-hole 115.

The fasteners 111 can be manipulated to selectively lock and unlock the angular position of the distal end portion 105 of the longitudinal support 104 relative to the longitudinal axis 116. To fix or lock the angular position of the distal end portion 105 of the longitudinal support 104 relative to the longitudinal axis 116, the fasteners 111 can be tightened to clamp the distal end portion 105 between the upper surface of the base 102 and a clamping plate 117. The clamping plate 117 includes a pair of holes arranged to receive the fasteners 111. To adjust the angular position of the distal end portion 105 of the longitudinal support 104 relative to the longitudinal axis 116, the fasteners 111 can be loosened to unclamp the distal end portion 105 between the base 102 and the clamping plate 117, which, in turn, allows the distal end portion 105 to move along the seat 107.

The base 102 and/or distal end portion 105 can include one or more indicators 151 that communicate to a user or clinician what angle S the longitudinal support 104 is at. This permits the clinician to objectively know the current angulation of the longitudinal support 104 and/or keep a record if desired. If subsequent changes are made, the clinician can track the changes and effects over time.

Optionally, the seat 107 defines a protrusion 121 arranged to interact with a corresponding groove on an outer surface of the distal end portion 105 of the longitudinal support 104. When the distal end portion 105 is attached to the base 102, the interaction between the protrusion 121 and the corresponding groove help prevents the distal end portion 105 from rotating on the base 102 around the fasteners 111, enhancing rotational stability.

An adaptor 101 is attachable to a bottom surface of the base 102. The adaptor 101 is adapted to be attached to a prosthetic limb or prosthesis such as a prosthetic pylon or foot and is made from a substantially rigid material to support the weight or load placed on the prosthetic limb. The adaptor 101 is shown as a female adaptor but can be a male adaptor or any other suitable attachment adaptors.

With reference to FIGS. 11-14, alternative embodiments of the base shown in FIGS. 1-10 are illustrated. The alternative bases may be arranged to adjust the alignment and/or circumference of the adjustable socket system 100. FIG. 11 illustrates a base 202 including a bottom surface defining a plurality of attachment holes 203 for connecting a prosthetic adaptor 201 to the base 202. The attachment holes 203 are arranged in a selected pattern so that an adaptor 201 can be attached to the base 202 in a number of different positions. This beneficially allows a user or clinician to customize alignment of the adjustable socket system 100 relative to a prosthetic device attached to the adaptor 201.

As shown by example in FIG. 12, the base 102 can be attached to a prosthetic connector system 250 for aligning a prosthetic limb or a prosthesis on the adjustable socket system 100. The prosthetic connector system 250 includes a plate 252 and a prosthetic adaptor 254 for connecting the adjustable socket system 100 to a prosthetic limb. The plate 252 is attachable to the base 102 via fasteners and includes a plurality of attachment holes 256 for attaching the prosthetic adaptor 254 to the plate 252. The attachment holes 256 are arranged such that the position of the prosthetic adaptor 254 on the plate 252 can be varied to adjust the position of the prosthetic limb relative to the adjustable socket system 100. This beneficially allows a user or clinician to customize alignment of the adjustable socket system 100 relative to the prosthetic limb. Further, the prosthetic connector system 250 can be an add-on module or accessory sold separately from the adjustable socket systems of the present disclosure.

FIGS. 12A-12G illustrate yet another embodiment of a prosthetic connector system 260 for connecting a prosthesis to a prosthetic socket system including a prosthetic socket. It will be appreciated that the prosthetic socket can comprise an adjustable prosthetic socket or a conventional prosthetic socket.

Figure 12A:
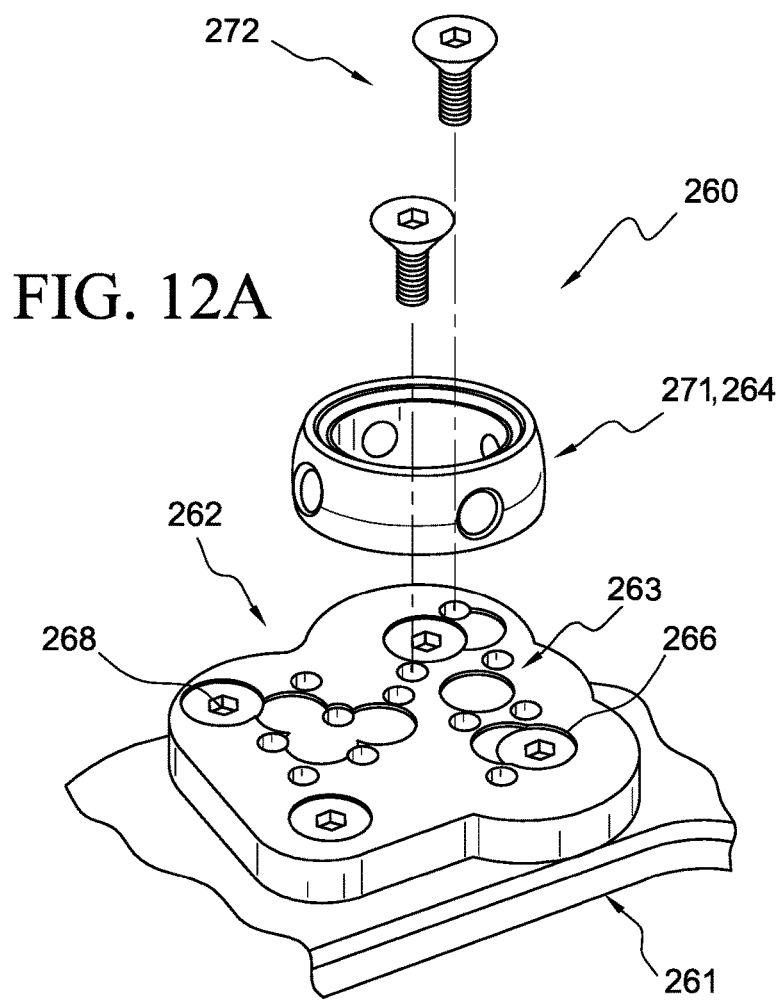
FIG. 12A is an exploded view of a prosthetic connector system according to an embodiment.

As seen in FIG. 12A, the prosthetic connector system 260 includes a plate 262 and a component 271 removably attachable to an attachment surface 263 of the plate 262. The component 271 can be arranged for connecting the prosthetic socket to the prosthesis. For instance, the component 271 can comprise a prosthetic adaptor 264. In other embodiments, the component 271 can comprise a plate, a body, or any other structure. According to a variation, the component 271 can be integral to the prosthesis.

In an embodiment, the plate 262 can comprise a shift plate or an offset plate configured such that an alignment between the prosthesis and the prosthetic socket can be selectively varied. The plate 262 includes a plurality of mounting holes 266 arranged for receiving a first plurality of fasteners 268 to attach the plate 262 to a base or distal part 261 of the prosthetic socket. The mounting holes 266 may be arranged in a standard 4-hole pattern such that the prosthetic connector system 260 can be used with the adjustable socket system of the present disclosure and/or a conventional socket system including a 4-hole component.

Figure 12B:
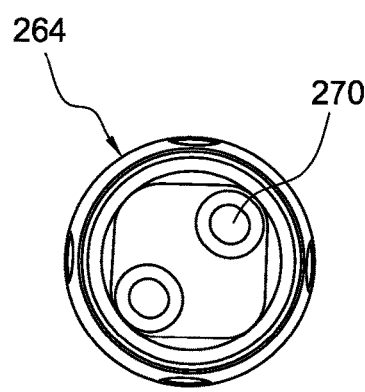
FIG. 12B is a bottom view of the prosthetic adaptor of FIG. 12A.

Referring to FIGS. 12A and 12B, the prosthetic adaptor 264 includes a plurality of attachment holes 270 arranged for receiving a second plurality of fasteners 272 to attach the prosthetic adaptor 264 to the attachment surface 263 of the plate 262. The second fasteners 272 can comprise a pair of fasteners and the attachment holes 270 can comprise a pair of attachment holes. The prosthetic adaptor 264 is shown comprising a female adaptor but can be any prosthetic component suitable to connect a prosthetic socket to a prosthesis. Optionally, the attachment holes 270 have an elliptical configuration, beneficially allowing for an amount of rotational adjustment between the prosthetic adaptor 264 and the plate 262.

Figure 12C:
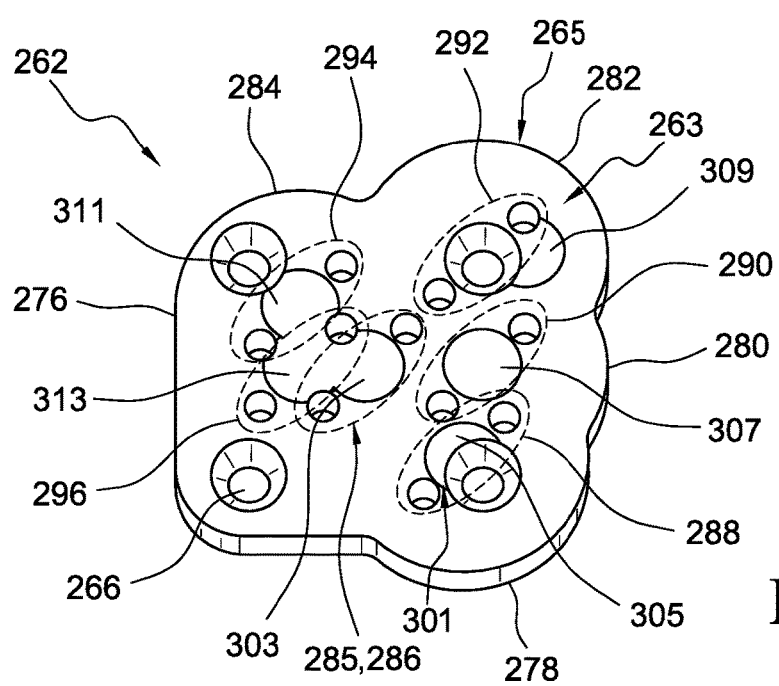
FIG. 12C is a perspective view of the plate of FIG. 12A.

Referring to FIG. 12C, the plate 262 can define an outer periphery 265 having an asymmetrical configuration contoured to substantially correspond to at least a portion of the prosthetic adaptor 264 in different positions on the plate 262. This beneficially allows the plate 262 to support and/or carry the prosthetic adaptor 264 in a greater number of positions using a smaller attachment surface than prior art adaptor plates. For instance, similar to the plate of the previous embodiment, the asymmetrical configuration of the outer periphery 265 of the plate 262 can include a plurality of sections having convexly curved contours. As seen, at least some of the plurality of sections can have different lengths and/or shapes. The attachment surface 263 has a planar configuration that is bounded by the outer periphery 265 having the asymmetrical configuration.

In an embodiment, the asymmetrical configuration of the outer periphery 265 includes a base section 276 having a rounded rectangular contour that transitions into a first section 278 having a convexly curved contour. The first section 278 transitions into a second section 280 having a convexly curved contour, which, in turn, transitions into a third portion 282 having a convexly curved contour. In the illustrated embodiment, the first section 278 is adjacent to the second section 280 and extends radially beyond the second section 278. The contour of the first portion 278 is different than the contour of the second portion 280. The first section 278 can have a greater length than the second section 280. The third section 282 extends radially beyond the second section 278. The size and/or shape of the third section 282 can be different than the size or shape of the second section 280.

The third section 282 transitions into a fourth section 284 having a convexly curved contour, which extends between the third section 282 and the base section 276. The third section 282 can have a different size than the fourth section 284. For instance, the third section 282 can extend radially beyond the fourth section 284. The size and/or shape of the third section 282 is different than the size and/or shape of the fourth section 284. For instance, the third section 282 has length greater than the second section 280 and the fourth section 284.

The asymmetrical configuration of the outer periphery 265 beneficially helps define one or more extended or designated areas on the plate 262 for supporting the prosthetic adaptor 264 when it is attached to different holes defined below. This allows the shape of the plate 262 to differ from one dedicated area to another, which, in turn, allows the plate 262 to accommodate a greater number of offset positions using a smaller surface area. The defined shapes or contours of the sections 278, 280, 282, and 284 also can lower the overall profile and weight of the plate 262 by eliminating at least some of the material forming the plate 262 in areas surrounding the prosthetic adaptor 264 when the prosthetic adaptor 264 is in one or more different positions on the plate 262. The plate 262 can be formed of steel, aluminum, molded plastic, or any other suitable material.

It will be appreciated that the asymmetrical configuration of the plate can comprise a cloud shape, a kidney shape, an asymmetrical heart shape, an asymmetrical leaf shape, an asymmetrical star shape, an asymmetrical triangular shape, or any other suitable shape. Further, the outer periphery of the plate can include any suitable number of sections having different shapes and/or sizes.

Referring still to FIG. 12C, the plate 262 defines a plurality of holes 285 configured to allow different positions and/or offsets for the prosthetic adaptor 264 on the plate 262. As such, the prosthetic adaptor 264 can be selectively attached to different ones of the holes 285 to vary an alignment between the distal part 261 or prosthetic socket and a prosthesis. The holes 285 can comprise placement holes or offset holes. In an embodiment, the holes 285 can include six pairs of placement holes 286, 288, 290, 292, 294, 296, providing six possible positions for the location of the prosthetic adaptor 264 on the plate 262. The combination of the holes 285 and asymmetrical periphery of the plate 262 however allows the plate 262 to have four different orientations with respect to the distal part 261 of the prosthetic socket, which, in turn, provides 21 positions or 20 offsets for the prosthetic adaptor 264 on the plate 262.

In the illustrated embodiment, the holes 285 comprise a central pair of holes 286 positioned relative to the mounting holes 266 such that when the prosthetic adaptor 264 is attached to the central pair of holes 286 the relative position between the prosthetic adaptor 264 and the distal part 261 of the prosthetic socket is the same in multiple orientations of the plate 262 on the distal part 261.

A first pair of holes 288 is located between the central pair of holes 286 and the first section 278 of the outer periphery 265. When the prosthetic adaptor 264 is attached to the first pair of holes 288, a contour of the first section 278 can substantially correspond to a portion of the outer shape of the prosthetic adaptor 264 positioned thereon, helping to lower the overall profile of the plate 262. In an embodiment, the first section 278 of the outer periphery 265 can generally extend along and below the prosthetic adaptor 264 protruding radially beyond the base section 276 of the outer periphery 265. This beneficially helps the plate 262 provide a larger radial offset for the prosthetic adaptor 264 on the attachment surface 263 when the prosthetic adaptor 264 is attached to the first pair of holes 288.

A second pair of holes 290 is located between the central pair of holes 286 and the second portion 280 of the plate 262. When the prosthetic adaptor 264 is attached to the second pair of holes 290, a contour of the second section 280 can substantially correspond to at least a portion of the outer shape of the prosthetic adaptor 264 positioned thereon, helping to lower the overall profile of the plate 262. The contoured fit of the prosthetic adaptor 264 on the plate 262 can be different on the first section 278 from the second section 280. For instance, the second section 280 is sized and shaped such that it extends along a different length of the outer diameter of the prosthetic adaptor 264 than the first section 278 of the outer periphery 265.

A third pair of holes 292 is located between the central pair of holes 286 and the third section 282 of the outer periphery 265. In an embodiment, at least one of the mounting holes 266 is located between the third pair of holes 292. When the prosthetic adaptor 264 is attached to the third pair of holes 292, a contour of the third section 282 of the outer periphery 265 can substantially correspond to at least a portion of the outer shape of the prosthetic adaptor 264 positioned thereon, helping to lower the overall profile of the plate 262. The third section 282 extends radially beyond both the base section 276 and the fourth section 284 of the plate 262, facilitating a larger radial offset for the prosthetic adaptor 264 when attached to the third pair of holes 292. For instance, at least one of the third pair of holes 292 can be located radially beyond the fourth section 284 of the outer periphery 265, facilitating a larger or alternative offset for the prosthetic adaptor 264.

A fourth pair of holes 294 is located between the central pair of holes 286 and the fourth section 284 of the outer periphery 265. When the prosthetic adaptor 264 is attached to the fourth pair of holes 294, a contour of the fourth section 284 can substantially correspond to at least a portion of the outer shape of the prosthetic adaptor 264 positioned thereon. The fourth section 284 is located radially inward relative to the third section 282, beneficially reducing the surface area of the attachment surface 263. A fifth pair of holes 296 is located between the central pair of holes 286 and the base section 276 of the plate 262.

As noted above, the combination of the holes 285 and the irregular, asymmetrical outer periphery 265 of the plate 262 allows the plate 262 to have four different orientations with respect to the distal part 261 of the prosthetic socket, which, in turn, provides 21 different positions for the prosthetic adaptor 264 on the plate 262. For example, FIG. 12D shows the prosthetic adaptor 264 in different positions on the plate 262 in a first orientation. When the plate 262 is in the first orientation and the prosthetic adaptor 264 is attached to the third pair of holes 292 (shown in FIG. 12C), the prosthetic adaptor 264 is placed in a first position 321. When the plate 262 is in the first orientation and the prosthetic adaptor 264 is attached to the second pair of holes 290 (shown in FIG. 12C), the prosthetic adaptor 264 is placed in a second position 323 that is different from the first position 321. When the plate 262 is in the first orientation and the prosthetic adaptor 264 is attached to the first pair of holes 288 (shown in FIG. 12C), the prosthetic adaptor 264 is placed in a third position 325 that is different from the other positions.

When the plate 262 is in the first orientation and the prosthetic adaptor 264 is attached to the central pair of holes 286 (shown in FIG. 12C), the prosthetic adaptor 264 is placed in a base position 319. When the plate 262 is in the first orientation and the prosthetic adaptor 264 is attached to the fifth pair of holes 296 (shown in FIG. 12C), the prosthetic adaptor 264 is placed in a fourth position 327 that is distinct from the other positions. When the plate 262 is in the first orientation and the prosthetic adaptor 264 is attached to the fourth pair of holes 294 (shown in FIG. 12C), the prosthetic adaptor 264 is placed in a fifth position 329 that is distinct from the other positions.

FIG. 12E shows the prosthetic adaptor 264 in different positions on the plate 262 when the plate 262 is in a second orientation turned about 90 degrees from the first orientation. When the plate 262 is in the second orientation and the prosthetic adaptor 264 is attached to the third pair of holes 292 (shown in FIG. 12C), the prosthetic adaptor 264 is located in a sixth position 331 that is different from the other positions. When the plate 262 is in the second orientation and the prosthetic adaptor 264 is attached to the second pair of holes 290 (shown in FIG. 12C), the prosthetic adaptor 264 is placed in a seventh position 333 that is distinct from the other positions. When the plate 262 is in the second orientation and the prosthetic adaptor 264 is attached to the first pair of holes 288 (shown in FIG. 12C), the prosthetic adaptor 264 is placed in an eighth position 335 that is different from the other positions.

When the plate 262 is in the second orientation and the prosthetic adaptor 264 is attached to the central pair of holes 286 (shown in FIG. 12C), the prosthetic adaptor 264 is located in the base position 319. In the second orientation, the prosthetic adaptor 264 attached to the central pair of holes 286 is in the same position as in the first orientation. When the plate 262 is in the second orientation and the prosthetic adaptor 264 is attached to the fifth pair of holes 296 (shown in FIG. 12C), the prosthetic adaptor 264 is located in a ninth position 337 that is different from the other positions. When the plate 262 is in the second orientation and the prosthetic adaptor 264 is attached to the fourth pair of holes 294 (shown in FIG. 12C), the prosthetic adaptor 264 is located in a tenth position 339 that is different from the other positions.

FIG. 12F shows the prosthetic adaptor 264 in different positions on the plate 262 when the plate 262 is in a third orientation. The third orientation can be turned about 180 degrees from the first orientation. When the plate 262 is in the third orientation and the prosthetic adaptor 264 is attached to the third pair of holes 292 (shown in FIG. 12C), the prosthetic adaptor 264 is located in an eleventh position 341 that is different from the other positions. When the plate 262 is in the third orientation and the prosthetic adaptor 264 is attached to the second pair of holes 290 (shown in FIG. 12C), the prosthetic adaptor 264 is located in a twelfth position 343 different from the other positions. When the plate 262 is in the third orientation and the prosthetic adaptor 264 is attached to the first pair of holes 288 (shown in FIG. 12C), the prosthetic adaptor 264 is located in a thirteenth position 345 that is different from the other positions.

When the plate 262 is in the third orientation and the prosthetic adaptor 264 is attached to the central pair of holes 286 (shown in FIG. 12C), the prosthetic adaptor 264 is located in the base position 319. As such, the prosthetic adaptor 264 attached to the central pair of holes 286 in the third orientation is in the same position as in the first orientation and the second orientation. When the plate 262 is in the third orientation and the prosthetic adaptor 264 is attached to the fifth pair of holes 296 (shown in FIG. 12C), the prosthetic adaptor 264 is located in a fourteenth position 347 that is different from the other positions. When the plate 262 is in the third orientation and the prosthetic adaptor 264 is attached to the fourth pair of holes 294 (shown in FIG. 12C), the prosthetic adaptor 264 is located in a fifteenth position 349 that is different from the other positions.

FIG. 12G shows the prosthetic adaptor 264 in different positions on the plate 262 when the plate 262 is in a fourth orientation. The fourth orientation can be turned about 270 degrees from the first orientation. When the plate 262 is in the fourth orientation and the prosthetic adaptor 264 is attached to the third pair of holes 292 (shown in FIG. 12C), the prosthetic adaptor 264 is located in a sixteenth position 351 that is different from the other positions. When the plate 262 is in the fourth orientation and the prosthetic adaptor 264 is attached to the second pair of holes 290 (shown in FIG. 12C), the prosthetic adaptor 264 is located in a seventeenth position 353 that is different from the other positions. When the plate 262 is in the fourth orientation and the prosthetic adaptor 264 is attached to the first pair of holes 288 (shown in FIG. 12C), the prosthetic adaptor 264 is located in an eighteenth position 355 that is different from the other positions.

When the plate 262 is in the fourth orientation and the prosthetic adaptor 264 is attached to the central pair of holes 286 (shown in FIG. 12C), the prosthetic adaptor 264 is located in the base position 319. As such, the prosthetic adaptor 264 attached to the central pair of holes 286 in the fourth orientation is in the same position as in the first orientation, the second orientation, and the third orientation. When the plate 262 is in the fourth orientation and the prosthetic adaptor 264 is attached to the fifth pair of holes 296 (shown in FIG. 12C), the prosthetic adaptor 264 is located in a nineteenth position 357 that is different from the other positions. When the plate 262 is in the fourth orientation and the prosthetic adaptor 264 is attached to the fourth pair of holes 294 (shown in FIG. 12C), the prosthetic adaptor 264 is located in a twentieth position 359 that is different from the other positions.

The plate 262 can thus provide 21 different positions for the prosthetic adaptor 264 on the plate 262 in four different orientations with respect to the distal part 261 of the prosthetic socket. Further, the irregular, asymmetrical shape of the outer periphery 265 can substantially correspond to the prosthetic adaptor 264 in different positions on the plate 262, using a smaller surface area than prior art adaptor plates to enhance the number of offset positions on the plate 262. It will also be appreciated that by changing the shape of the plate 262, the positions of the prosthetic adaptor 264 on the plate 262 and orientations of the plate 262 may be varied. Similarly, by placing the holes 285 in more or fewer locations in the plate 262 more or fewer offset options may be achieved. Further, while the prosthetic adaptor 264 is described having a pair of attachment holes, it will be appreciated that in other embodiments, the prosthetic adaptor 264 can include one, three, or any other suitable of attachment holes arranged to align with corresponding holes 285 in the plate 262.

Referring again to FIG. 12C, the plate 262 may include one or more indicators 301 to provide visual guidelines to a user or clinician regarding the offset of the prosthetic adaptor 264. For instance, the one or more indicators 301 can include a base position indicator 303 associated with the central pair of holes 286 marked as "0/0." The base position indicator 303 indicates to the user or the clinician that when the prosthetic adaptor 264 is attached to the central pair of holes 286 and a prosthesis is attached to the prosthetic adaptor 264, the position of the prosthesis relative to the distal part 261 or the prosthetic socket is the same in the first, second, third, and fourth orientations of the plate 262.

A first offset indicator 305 can be associated with the first pair of holes 288. The first offset indicator 305 indicates to the user or the clinician that when the prosthetic adaptor 264 is attached to the first pair of holes 288, the position of the prosthesis relative to the central pair of holes 286 is offset a first distance from the central pair of holes 286 in two directions. It will be appreciated that the directions of the offsets will vary based on the orientation of the plate 262. In an embodiment, the first offset indicator 305 is marked "15/15" such that the corresponding offset is 15 mm in two directions from the central pair of holes 286, one direction perpendicular to the other.

A second offset indicator 307 can be associated with the second pair of holes 290. The second offset indicator 307 indicates to the user or the clinician that when the prosthetic adaptor 264 is attached to the second pair of holes 290, the position of the prosthesis is aligned in one direction with the central pair of holes 286 and is offset a second distance from the central pair of holes 286 in another direction. It will be appreciated that the direction of the offset will vary based on the orientation of the plate 262. In an embodiment, the second offset indicator 307 is marked "0/20" such that the corresponding offset is 20 mm in one direction from the central pair of holes 286.

A third offset indicator 309 can be associated with the third pair of holes 292. The third offset indicator 309 indicates to the user or the clinician that when the prosthetic adaptor 264 is attached to the third pair of holes 292, the position of the prosthesis is offset a third distance from the central pair of holes 286 in two directions. It will be appreciated that the directions of the offset will vary based on the orientation of the plate 262. In an embodiment, the third offset indicator 309 is marked "18/18" such that the corresponding offset is 18 mm in two directions from the central pair of holes 286, one direction perpendicular to the other.

A fourth offset indicator 311 can be associated with the fourth pair of holes 294. The fourth offset indicator 311 indicates to the user or the clinician that when the prosthetic adaptor 264 is attached to the fourth pair of holes 294, the position of the prosthesis is offset a fourth distance from the central pair of holes 286 in two directions. It will be appreciated that the directions of the offset will vary based on the orientation of the plate 262. In an embodiment, the fourth offset indicator 311 is marked "10/10" such that the corresponding offset is 10 mm in two directions from the central pair of holes 286, one direction perpendicular to the other.

A fifth offset indicator 313 can be associated with the firth pair of holes 296. The fifth offset indicator 313 indicates to the user or the clinician that when the prosthetic adaptor 264 is attached to the fifth pair of holes 296, the position of the prosthesis is aligned in one direction with the central pair of holes 286 and is offset the fourth distance from the central pair of holes 286 in another direction. The offset can vary based on the orientation of the plate 262. In an embodiment, the fifth offset indicator 313 is marked "0/10" such that the corresponding offset is 10 mm from the central pair of holes 286 in one direction.

The one or more indicators 301 thus provide simple to use visualization guidelines for a user or clinician, facilitating use of the prosthetic connector system 260. It will be appreciated that the one or more indicators 301 can be laser cut, engraved, and/or printed on the attachment surface 263.

Figure 13:
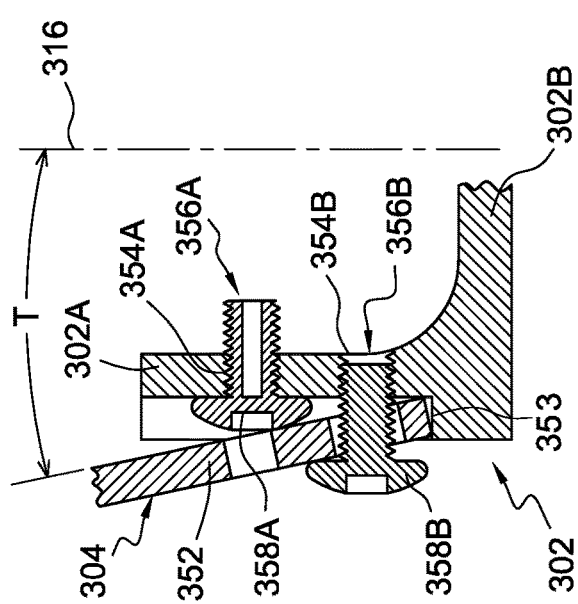
FIG. 13 is a cross section of a longitudinal support and base according to another embodiment.

In other configurations of the base, the connection between the longitudinal supports 104 and the base can be adjusted. FIG. 13 illustrates a base 302 having a base segment 302B and one or more connecting segments 302A extending upwardly from the base segment 302B arranged to be connected to a distal end portion 352 of the longitudinal support 304. The connecting segment 302A defines two holes 354A, 354B along the longitudinal axis of the connecting segment 302A for receiving a pair of fasteners 356A, 356B for attaching the distal end portion 352 of the longitudinal support 304 to the base 302. Optionally, an outer surface of the connecting segment 302A can define a seat 353 arranged to receive the distal end portion 352 of the longitudinal support 304. It will be appreciated that the base 302 and the longitudinal support 304 can be made of any suitable material such as carbon fiber, plastic, metal, or combinations thereof.

The first fastener 356A can be threadedly attached to the hole 354A such that a head portion 358A of the first fastener 356A engages the inner surface of the distal end portion 352 of the longitudinal support 304. The second fastener 356B can be threadedly attached to the hole 354B such that a head portion 358B of the second fastener 356B engages the outer surface of the distal end portion 352 of the longitudinal support 304. The longitudinal support 304 is thus attached to the base 302 by the second fastener 356B, and the head portion 358A of the first fastener 356A forms a pivot about which the distal end portion 352 can pivot.

The position of the first and second fasteners 356A, 356B along the longitudinal axes of the holes 354A, 354B can be varied to adjust an angle T defined between the distal end portion 352 and a longitudinal axis 316. For instance, the angle T can be increased by tightening the first fastener 356A and/or loosening the second fastener 356B in the holes 354A, 354B. The angle T can be decreased by loosening the first fastener 356A and/or tightening the second fastener 356B. This allows the longitudinal support 304 to be set at different angles relative to the longitudinal axis 316 for adjustment, improving the fit and support of the adjustable socket system 100.

Figure 14A:
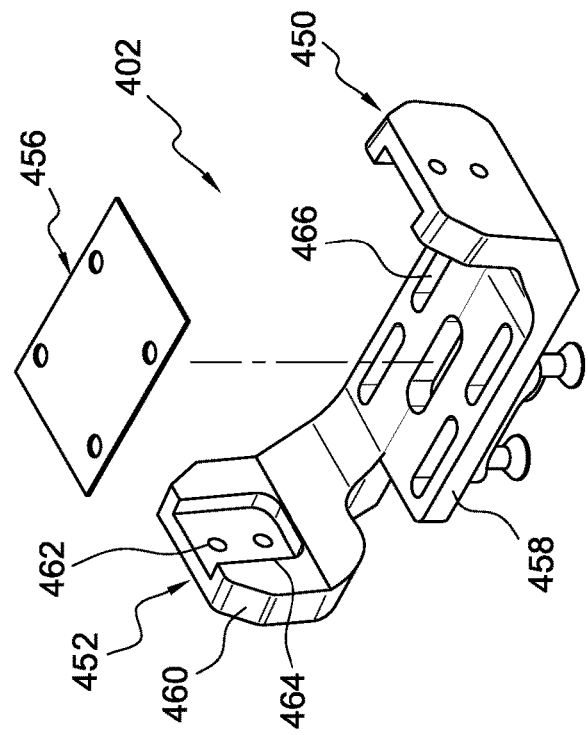
FIG. 14A is a perspective view of a base according to another embodiment.
Figure 14B:
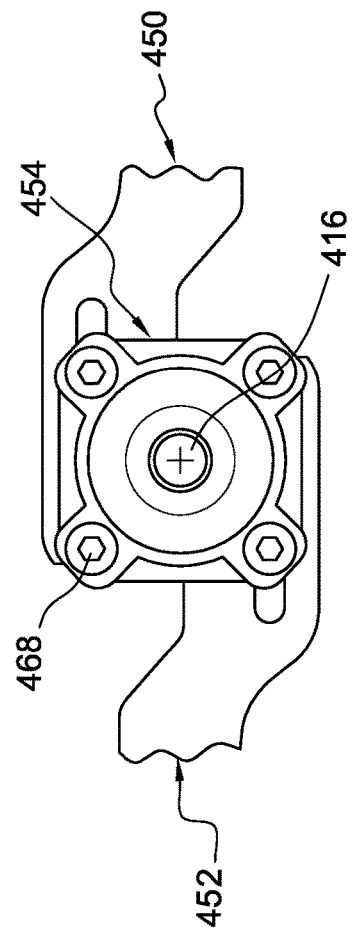
FIG. 14B is a bottom view of the base of FIG. 14A.

FIGS. 14A and 14B illustrate a base 402 including a first component 450, a second component 452, an adaptor 454, and a mounting plate 456. The adaptor 454 is adapted to be attached to a prosthesis and is shown as a male adaptor but can be a female adaptor or any other suitable adaptor. The first and second components 450, 452 are located between the adaptor 454 and the mounting plate 456. The first and second components 450, 452 are radially adjustable relative to one another to vary a circumference of the adjustable socket system 100. In an embodiment, the first component 450 slidably engages the second component 452 and can be locked into different positions with respect to the second component 452.

The base 402 forms an anatomically shaped receiving space adapted to receive the distal end of a residual limb. Each of the first and second components 450, 452 includes a base segment 458 and connecting segments 460 extending upwardly from the base segment 458. One of the connecting segments 460 can connect to a medial support and the other can connect to a lateral support. The connecting segments 460 define a plurality of openings 462 arranged to receive fasteners for attaching the supports to the base 402. The connecting segments 460 may have a width greater than the base segments 458, increasing the contact area between the supports and the base 402. Optionally, an inner surface of the connecting segments 460 defines a seat 464 arranged to receive a distal end portion of the support.

Each base segment 458 defines a plurality of elongated holes 466. A plurality of fasteners 468 extend through the elongated holes 466 and connect the adaptor 454 to the mounting plate 456 such that the base segments 458 are located between the adaptor 454 and the mounting plate 456. In use, the fasteners 468 can be loosened such that the base segments 458 can radially slide between the adaptor 454 and the mounting plate 456 relative to a longitudinal axis 416, which, in turn, adjusts the circumference of the adjustable socket system 100 via adjustment of the base 402.

The fasteners 468 can be tightened such that the base segments 458 are clamped between the adaptor 454 and the mounting plate 456, locking or fixing the radial position of the base segments 458 relative to the longitudinal axis 416. This advantageously allows the circumference of the base 402 to be continuously adjustable within a range defined by the elongated holes 466.

FIGS. 15A and 15B illustrate a distal insert 550 that can be included with an adjustable socket system 500 of the present disclosure. The distal insert 550 is arranged to be connected to a distal end of a prosthetic liner and positioned on a base 502 of the adjustable socket system 500. The distal insert 550 can be integral to the liner or attached to the liner. The distal insert 550 defines an outer peripheral surface 552 and can be attached to the liner in any suitable manner. As seen, the outer surface 552 can define a plurality of ribs or corrugations 554 adapted to increase friction between the distal insert 550 and one or more shell components of the adjustable socket system 500. In an embodiment, the distal insert 550 can include one or more materials with a high coefficient of friction such as elastomeric polymers to increase friction between the distal insert 550 and the shell components.

According to a variation, the distal insert 550 communicates information to a user or clinician. For instance, a distal region of the outer surface 552 can include at least one colored band 556. The colored band 556 can be a bright color such as yellow, orange, or hot pink. When the liner is correctly positioned on the base 502, the colored band 556 can be visible through an observation window 558 at or near the base 502. This advantageously communicates correct positioning of the liner in the adjustable socket system 500. When the colored band 556 is not visible through the observation 558, its absence communicates incorrect positioning of the liner in the adjustable socket system 500.

With reference to FIGS. 16-19, alternative embodiments of the adjustable socket system shown in FIGS. 1-15 are illustrated. The alternative adjustable socket systems are radially adjustable and may include one or more shell components that are adjustable in length to better fit and support a residual limb.

As shown in the example in FIG. 16, an adjustable socket system 600 includes a base 602 and a plurality of longitudinal supports 604 connected to the base 602. The shell components and tightening system are not shown for ease of reference. The base 602 can include a distal cup 650 arranged to support a distal end of a residual limb and the longitudinal supports 604 can include a medial support 604A and a lateral support 604B, both arranged to pivot about a mid-region of the adjustable socket system 600. The longitudinal supports 604 can be formed of the same materials as the longitudinal supports 104.

The lateral support 604B has a multi-part configuration including a distal segment 652, a proximal segment 654, and a brim component 656 attached to the proximal segment 654. A distal end of the distal segment 652 is attached to the base 602 and a proximal end of the distal segment 652 forms a pivoting connection 658 with the proximal segment 654. The proximal segment 654 is pivotally attached to the distal segment 652 via the pivoting connection 658.

The proximal segment 654 overlaps the distal segment 652 in a longitudinal direction. A seat or receptacle 662 is located on the inner surface of the distal segment 652 for accommodating the distal end of the proximal segment 654. The seat 662 limits the distal end of the proximal segment 654 from sliding sideways on the distal segment 652.

The medial support 604A is arranged similar to the lateral support 604B including a distal segment 664 fixedly attached to the base 602, a proximal segment 666 attached to the distal segment 664 via pivoting connection 668, and a seat 672.

In use, the proximal segments 654, 666 can independently rotate about the pivoting connections 658, 668 to radially reposition the distal and proximal ends of the proximal segments 654, 666 relative to a longitudinal axis 616 of the adjustable socket system 600. For instance, as a residual limb engages the distal ends of the proximal segments 654, 666 upon donning, the radial position of the proximal ends of the proximal segments 654, 666 rotate toward the longitudinal axis 616, loading the proximal region of the residual limb. This adjustment can help improve shape capture of the adjustable socket system 600 and adjustment of the circumference of the adjustable socket system 600. According to a variation, the distal end of at least one of the proximal segments 654, 666 is resiliently biased or spring loaded in a direction toward the longitudinal axis 616.

Figure 17:
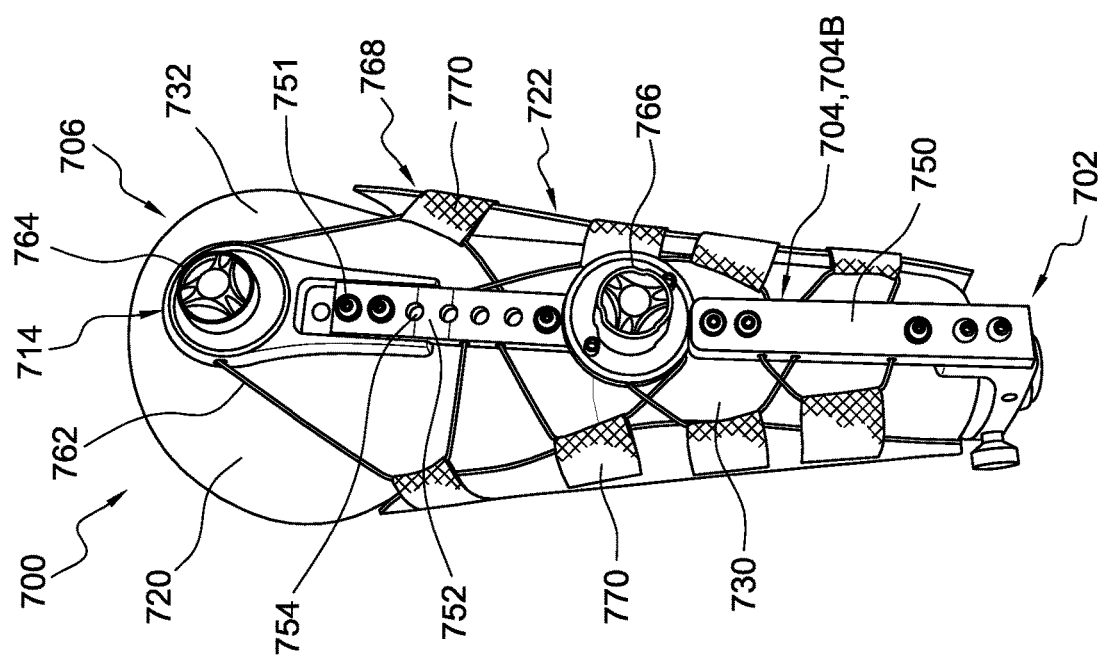
FIG. 17 is a side view of an adjustable socket system according to another embodiment.

FIG. 17 illustrates an adjustable socket system 700 according to yet another embodiment including a base 702, a plurality of longitudinal supports 704 connected to the base 702, and a plurality of shell components 706 including first and second shell components 722, 720 connected to the longitudinal supports 704. Like in other embodiments, the adjustable socket system 700 is movable between an open configuration and a closed configuration via a tightening system 714.

The longitudinal supports 704 include at least one support 704B having a segmented configuration that can facilitate a length adjustment of at least one of the shell components 706. For instance, the second shell component 720 includes distal and proximal parts 730, 732 and the longitudinal support 704B includes a distal segment 750 removably attached to the base 702, and a proximal segment 752 removably attached to the distal part 750. A proximal part 732 of the second shell component 720 is attached to the proximal segment 752 and the distal part 730 of the second shell component 720 is attached to the distal segment 750 and/or the base 702.

The distal and proximal segments 750, 752 define a plurality of through holes 754 along a longitudinal axis of the lateral support 704B. The through holes 754 are adapted so that the proximal segment 752 can be attached at different locations along the length of the distal segment 750 with one or more fasteners 751, which, in turn, longitudinally displaces the proximal part 732 of the second shell component 720 relative the distal part 730. It will be appreciated that a medial support can be configured similar to the lateral support 704B and a first shell component 722 can be configured similar to the second shell component 720.

The tightening system 714 includes at least one tensioning element 762 operatively linked to first and second tensioners 764, 766. The first and second tensioners 764, 766 are shown as dial tensioners but can be any suitable tensioning mechanisms. The first tensioner 764 can be attached to a proximal portion of the lateral support 704B and the second tensioner 766 can be attached to an intermediate region of the lateral support 704B. The at least one tensioning element 762 can be formed of line, wire, cord, or any other suitable element.

The at least one tensioning element 762 is connected to the first and second tensioners 764, 766 and routed through a plurality of guides 768 located toward the lateral aspect of the system 700. The guides 768 comprise loops of fabric 770 on the first shell component 722. The fabric loops 770 can be integrated with or attached to the first shell component 722. Using fabric loops 770 as guides for the at least one tensioning element 762 allows for a degree of distal and proximal movement of the at least one tensioning element 762 relative to the first shell component 722 during use, which, in turn, allows the at least one tensioning element 762 better accommodate movement of the residual limb during a user's gait, making the adjustable socket system 700 more comfortable.

The fabric loops 770 can be attached to the first shell component 722 in any suitable manner. For example, the fabric loops 770 can be attached to an outer fabric layer of the second shell component 720 comprising a robust or durable material. The fabric loops 770 can be attached to a semi-rigid body of the first shell component 722 for reinforcement. According to a variation, the fabric loops 770 can include stitching to strengthen the fabric loops 770 and/or define a small channel configured to receiving the at least one tensioning element 762. This can help direct the at least one tensioning element 762 between the edges of the first shell component 722. The fabric loops 770 can be non-elastic or elastic and can comprise any suitable number of loops.

Figure 18:
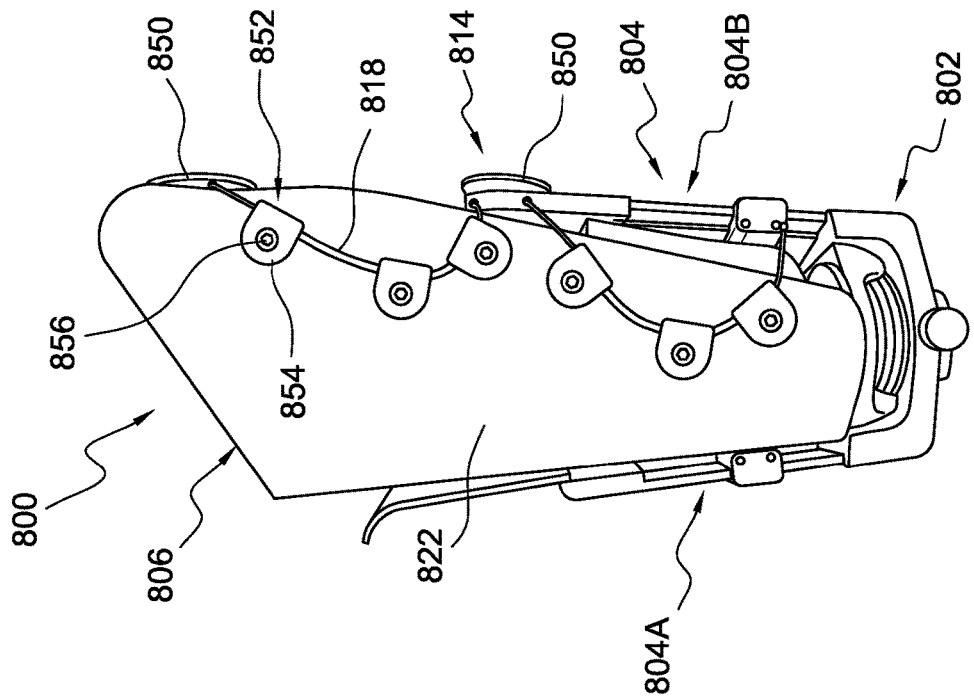
FIG. 18 is a front view of an adjustable socket system according to another embodiment.

FIG. 18 illustrates an adjustable socket system 800 according to another embodiment including a base 802, a plurality of longitudinal supports 804 connected to the base 802, a plurality of shell components 806 operatively connected to the longitudinal supports 804, and a tightening system 814 for radially adjusting the adjustable socket system 800 between the open and closed configurations.

The longitudinal supports 804 include a medial support 804A and a lateral support 804B, but can be in any suitable configuration. At least one of the longitudinal supports 804 is pivotally attached to the base 802. In other embodiments, at least one of the longitudinal supports 804 has a non-articulating configuration adapted to bend or flex to adjust or vary the receiving volume of the adjustable socket system 800.

The tightening system 814 includes one or more tensioning elements 818 operatively linked to one or more tensioners 850 and connected to a lateral aspect of the adjustable socket system 800. The one or more tensioning elements 818 are routed through a plurality of guides 852 between the shell components 806 and the one or more tensioners 850.

The guides 852 are separate guide members 854 attached to the outer surface of a shell component 806 via fasteners 856. The connection between the guides 852 and the fasteners 856 can be such that the guides 852 rotate about the fasteners 856 when the one or more tensioning elements 850 are tensioned and loosened by the one or more tensioners 850, which, in turn, allows the relationship between the one or more tensioning elements 850 and a first shell component 822 to shift during use. This beneficially helps accommodate movement of the residual limb during a user's gait, making the adjustable socket system 800 more comfortable.

The removable attachment of the guide members 854 to the shell component 806 can also permit the guide members 854 to be repositioned on the shell component 806 based on the needs of the user or a particular indication.

Figure 19:
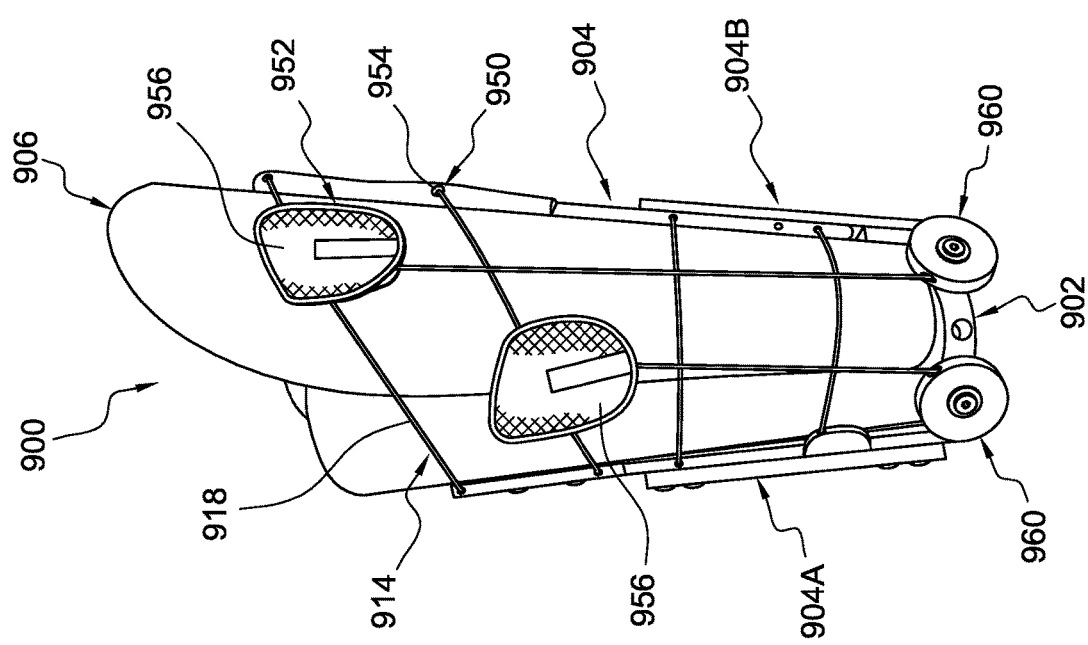
FIG. 19 is a front view of an adjustable socket system according to another embodiment.

FIG. 19 illustrates yet another embodiment of an adjustable socket system 900 including a base 902, a plurality of longitudinal supports 904 comprising a lateral support 904B and medial support 904A connected to the base 902, a plurality of shell components 906 operatively connected to the longitudinal supports 904, and a tightening system 914 arranged to radially adjust the adjustable socket system 900 between an open configuration and a closed configuration.

The shell components 906 include a first shell component configured to wrap around and engage at least the medial aspect of the residual limb and a second shell component configured to wrap around and engage at least a lateral aspect of the residual limb.

The tightening system 914 includes at least one tensioning element 918, guides 950, and at least one tensioner 952 operatively connected to the at least one tensioning element 918. The at least one tensioning element 918, which is shown as a cable or wire, is looped around the adjustable socket system 900 through the guides 950 on or near the lateral and medial supports 904A, 904B. The guides 950 can comprise through holes 954 in the longitudinal supports 904.

The at least one tensioner 952 comprises one or more handles 956 including a hook or loop material that allows the handle 956 to selectively attach to an outer surface of at least one of the shell components 906, which, in turn, locks the position of the at least one tensioning element 918 and maintains tension, if any, in the at least one tensioning element 918.

At least some of the guides 950 on the medial support 904A and the lateral support 904B are longitudinally offset to loop the at least one tensioning element 918 through the guides 950 in a generally spiraling fashion along the length of the adjustable socket system 900. From the guides 950, the at least one tensioning element 918 passes through a plurality of pulley assemblies 960 connected to the base 902. The pulley assemblies 960 reduce the amount of force needed to move the adjustable socket system 900 to the closed configuration.

In use, a user can grip one or more of the handles 956 and pull on the at least one tensioning element 918, which, in turn, tensions the at least one tensioning element 918 and moves the adjustable socket system 900 toward the closed configuration. When a desired level of tension or loading in the adjustable socket system 900 is achieved, the user can attach the one or more handles 956 to the shell components 906, maintaining the tension in the at least one tensioning element 918. The pulley assemblies 960 increase a travel distance of the at least one tensioning element 918, decreasing the level of physical effort needed by the user to tension the at least one tensioning element 918. In other embodiments, the pulley assemblies 960 can be adapted to enable a user to apply a greater tension to the at least one tensioning element 918.

When the user desires to move the adjustable socket system 900 toward the open configuration or loosen the adjustable socket system 900, the user can detach the one or more handles 956 from the shell components 906, releasing the tension in the at least one tensioning element 918. The tightening system 914 thus provides an intuitive and simple manner for users with limited dexterity or cognition to adjust the fit of the adjustable socket system 900.

Figures 20A, 20B:
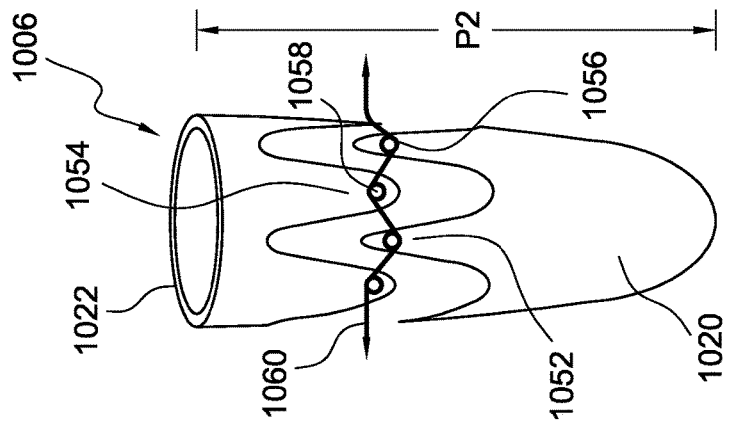
FIG. 20A is a side view of a shell component in a first predetermined length according to another embodiment of an adjustable socket system.
FIG. 20B is a side view of the adjustable socket system of FIG. 21A in a second predetermined length.

Alternative embodiments of shell components having an adjustable length are shown in FIGS. 20 and 21. FIGS. 20A and 20B shows a shell component 1006 including a distal shell component 1020 and a proximal shell component 1022. A proximal end portion 1050 of the distal shell component 1020 defines a first plurality of teeth 1052 arranged to mesh or interact with a second plurality of teeth 1054 defined on a distal end portion 1056 of the proximal shell component 1022. The first and second pluralities of teeth 1052, 1054 are shown generally elongated but can have any suitable configuration. The shell component 1006 can be made of the same or similar materials as the other shell components of the present disclosure.

The shell component 1006 is adjustable in length. The shell component 1006 is movable between a first predetermined length P1 in which the first and second teeth 1052, 1054 are substantially fully engaged and the distal and proximal shell components 1020, 1022 are longitudinally displaced toward one another, and a second predetermined length P2 in which the first and second teeth 1052, 1054 are at least partially disengaged and the distal and proximal shell components 1020, 1022 are longitudinally displaced away from one another.

A tightening system 1014 is adapted to move the shell component 1006 between the first and second predetermined lengths P1, P2. It will be appreciated that the tightening system 1014 can also be arranged to tighten the fit of an adjustable socket system on the residual limb as described herein. The tightening system 1014 includes a first plurality of guides 1056 positioned at or near the first plurality of teeth 1052, a second plurality of guides 1058 positioned at or near the second plurality of teeth 1054. The guides 1056, 1058 can be integral to shell component 1006 or attached to the shell components 1006.

A tensioning element 1060 is laced through the guides 1056, 1058 such that when the tensioning element 1060 is tensioned, the tensioning element 1060 pulls the proximal part 1022 away from the distal part 1020, moving the shell component 1006 toward the extended position. When the tension is released in the tensioning element 1060, the shell component 1006 can be arranged to automatically return to the default position.

The overall length of the shell component 1006 is thus continuously adjustable within a range defined by a length of the first and second pluralities of teeth 1052, 1054 and/or the tensioning element 1060. This continuous adjustability allows the length of the shell component 1006 to be adjusted in an infinite number of positions rather than being adjustable in discrete increments, providing greater versatility and functionality.

FIGS. 21A and 21B illustrate another shell component 1106 similar to the shell component 1006, except that the distal part 1120 and the proximal part 1122 are initially in the second predetermined length P2 (shown in FIG. 21A) in which the distal part 1120 and the proximal part 1122 are moved away from one another in a longitudinal direction. From the second predetermined length P2, the shell component 1106 is movable into first predetermined length P1 (shown in FIG. 21B) in which first and second pluralities of teeth 1152, 1154 are substantially fully engaged and the distal and proximal parts 1120, 1122 are moved together, reducing the length of the shell component 1106.

A tightening system 1114 is arranged to move the shell component 1106 between the first and second predetermined lengths P1, P2. The tightening system 1114 includes a tensioning element 1118 laced or threaded through a plurality of guides 1156, 1558 so that when the tensioning element 1118 is tensioned, the tensioning element 1118 moves the distal and proximal parts 1120, 1122 toward the first predetermined length P1. When the tension in the tensioning element 1118 is released, the shell component 1106 is arranged to automatically return to the second predetermined length P2.

A plurality of springs 1160 are disposed between the distal and proximal parts 1120, 1122. The springs 1160 are arranged to bias the shell component 1106 toward the second predetermined length P2.

Adjustable socket system embodiments of the present disclosure are radially adjustable between open and closed configurations. FIGS. 22-26 illustrate alternative examples of these systems that open and close to help secure the adjustable socket systems on a residual limb. FIGS. 22A and 22B illustrate an adjustable socket system 1200 including a prosthetic liner 1250 having a locking element 1252 corresponding to a slot 1254 defined on a longitudinal support 1204 or shell component 1206 of the adjustable socket system 1200. The locking element 1252 can comprise a locking ring 1258 or any other suitable structure.

Similar to other embodiments, the adjustable socket system 1200 moves between the open and closed configurations. As the adjustable socket system 1200 moves toward the closed configuration, the locking element 1252 locks into the slot 1254, counteracting a pull-out movement of the liner 1250 in a proximal direction from the adjustable socket system 1200. As the adjustable socket system 1200 moves toward the open configuration, the locking element 1252 releases from the slot 1254 as the supports 1204 and/or shell components 1206 move radially outward relative to the longitudinal axis of the adjustable socket system 1200. The locking element 1252 thus locks and releases with tightening and loosening of the adjustable socket system 1200.

FIGS. 23A-23C illustrate another adjustable socket system 1300 including a locking element 1352. The system 1300 comprises a prosthetic liner 1350 having one or more locking elements 1352 protruding from an outer surface of the liner 1350.

The locking elements 1352 can be a plurality of locking teeth 1358 arranged to selectively lock in corresponding holes 1354 defined in a longitudinal support 1304 and/or shell component 1306. As the adjustable socket system 1300 moves toward the closed configuration, the locking teeth 1358 lock into the holes 1354, counteracting a pull-out movement of the liner 1350 in a proximal direction from the adjustable socket system 1300. As the adjustable socket system 1300 moves toward the open configuration, the locking teeth 1358 release from the holes 1354 as the longitudinal supports 1304 and/or the shell components 1306 move radially outward relative to a longitudinal axis of the adjustable socket system 1300.

In an embodiment, the holes 1354 can be through holes such that when the locking teeth 1358 are locked in the holes 1354, the locking teeth 1358 protrude radially beyond the outer surface of the shell component 1306 and/or the longitudinal support 1304, providing visual feedback to a user. In other embodiments, as the locking teeth 1358 lock in and out of the holes 1354 they can provide audible and/or tactile feedback to a user.

FIG. 24 illustrates an adjustable socket system 1400 according to another embodiment, including a liner 1450 including a first plurality of locking teeth 1458 having a square shape arranged to interface with a second plurality of locking teeth 1460 defined by the support 1404 and/or the shell component 1406. As the adjustable socket system 1400 moves toward the closed configuration, the first plurality of locking teeth 1458 lock with the second plurality of locking teeth 1460, counteracting a pull-out movement of the liner 1450 in a proximal direction from the adjustable socket system 1400.

FIG. 25 illustrates an adjustable socket system 1500 similar to the system 1400 including a liner 1550 having a first plurality of teeth 1558. The first plurality of teeth 1558 have an angled configuration and the second plurality of teeth 1560 have a corresponding angled configuration.

FIG. 26 illustrates an adjustable socket system 1600 that includes a liner 1650 having a plurality of locking regions 1652 distributed circumferentially and extending longitudinally along the liner 1650. The locking regions 1652 can comprise strips 1654 can extend along the entire or a portion of a length of the liner 1650. The strips 1654 are arranged to interface with a corresponding structure on a longitudinal support or shell component to counteract a pull-out movement of the liner 1650 in a proximal direction from the adjustable socket system 1600.

The strips 1654 can include silicone adapted to mate with corresponding silicone on the inside of a longitudinal support of the adjustable socket system 1600. In other embodiments, the strips 1654 can include hook material arranged to mate with corresponding loop material on the adjustable socket system 1600. In yet other embodiments, the strips 1654 can include permanent magnets arranged form a magnetic attraction with ferromagnetic material on the adjustable socket system 1600. In other embodiments, the strips 1654 can include sticky material.

Adjustable socket system embodiments of the present disclosure thus provide improved support and fit over prior art systems. From its versatility in fitting and force distribution, the adjustable socket system embodiments can decrease pain, discomfort and soft tissue breakdown.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic connector system for use with a prosthetic socket having a distal end, the prosthetic connector system comprising:
   a monolithic and homogenous plate defining at least two pairs of holes and attachable to the distal end of the prosthetic socket;
   a component removably attachable to the plate via the at least two pairs of holes and arranged for connecting a prosthesis to the prosthetic socket,
   wherein the plate defines an outer periphery forming a predetermined asymmetrical configuration contoured to substantially correspond to at least a portion of the component when the component is selectively attached to the plate by one pair of said at least two pairs of holes, wherein the plate defines an attachment surface having a planar profile bounded by the outer periphery with said predetermined asymmetrical configuration;
   wherein the plate is positionable in at least first and second positions by rotating the plate in a direction normal to the planar profile of the plate, the at least two pairs of holes providing at least four orientations for the component relative to the distal end of the prosthetic socket among the first and second positions;

wherein the said at least two pairs of holes includes a central pair of holes arranged to provide a single position for the component relative to the distal end of the prosthetic socket;

wherein said at least two pairs of holes also includes a first pair of holes, and wherein a first offset indicator is associated with the first pair of holes, the first offset indicator is arranged to indicate a position of the first pair of holes offset a first distance from the central pair of holes in first and second directions perpendicular to one another;

wherein the predetermined asymmetrical configuration of the outer periphery is fixed and unchangeable, and the predetermined asymmetrical configuration comprises a plurality of defined sections having convexly curved contours, at least some of the plurality of sections having different lengths;

wherein the plurality of sections include a first section and a second section adjacent the first section, the first section extending radially beyond the second section.

2. The prosthetic connector system of claim 1, wherein the predetermined asymmetrical configuration of the outer periphery comprises a base section having a rounded rectangular contour extending between at least two of the sections.

3. The prosthetic connection system of claim 1, wherein a length of the first section is greater than a length of the second section.

4. The prosthetic connection system of claim 1, wherein the plurality of sections includes a third section adjacent to the second section, the third section protruding radially beyond the second section.

5. The prosthetic connection system of claim 4, wherein a length of the third section is greater than a length of the second section.

6. The prosthetic connector system of claim 5, wherein the length of the third section and the second section are different.

7. The prosthetic connector system of claim 1, wherein at least some of the convexly curved contours are arranged to substantially fit and support an outer diameter of the component when the component is attached to the plate by said one pair of said at least two pairs of holes.

8. The prosthetic connector system of claim 7, wherein the said one pair of said at least two pairs of holes is arranged to provide four different positions for the component relative to the distal end of the prosthetic socket when the plate is in four different orientations on the distal end of the prosthetic socket.

9. The prosthetic connector system of claim 1, wherein the component comprises a prosthetic adaptor defining a pair of attachment holes arranged for providing an amount of rotational adjustment between the prosthetic adaptor and the plate.

10. The prosthetic connector system of claim 9, wherein the attachment holes have an elliptical configuration.

11. The prosthetic connector system of claim 1, wherein the component comprises a female prosthetic adaptor.

12. A prosthetic connector system for use with a prosthetic socket having a distal end, the prosthetic connector system comprising:

a monolithic and homogenous plate defining a plurality of holes and attachable to the distal end of the prosthetic socket;

a prosthetic adaptor removably attachable to the plate via the holes and arranged for connecting a prosthesis to the prosthetic socket, wherein the plate defines an outer periphery forming a predetermined asymmetrical configuration comprising a plurality of convexly curved contours arranged to substantially correspond to at least a portion of the prosthetic adaptor when the prosthetic adaptor is attached to the plate via at least some of the holes;

wherein the plurality of holes includes six pairs of holes arranged to provide twenty one different positions for the prosthetic adaptor relative to the distal end of the prosthetic socket when the plate is in four different orientations on the distal end of the prosthetic socket;

wherein the plate defines a fixed and unchangeable outer periphery forming the predetermined asymmetrical configuration such that the outer periphery comprises a plurality of sections having convexly curved contours, at least some of the plurality of sections having different lengths;

wherein the plurality of sections include a first section and a second section adjacent the first section, the first section extending radially beyond the second section.

* * * * *